(12) United States Patent
St. Cyr et al.

(10) Patent No.: US 9,733,156 B2
(45) Date of Patent: Aug. 15, 2017

(54) SAMPLE PLATFORMS AND METHODS OF USING THEM

(71) Applicants: Paul L. St. Cyr, Shelton, CT (US); Michael L. DelVecchio, Stratford, CT (US)

(72) Inventors: Paul L. St. Cyr, Shelton, CT (US); Michael L. DelVecchio, Stratford, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 794 days.

(21) Appl. No.: 13/662,801

(22) Filed: Oct. 29, 2012

(65) Prior Publication Data

US 2014/0116161 A1    May 1, 2014

(51) Int. Cl.
*G01N 1/00* (2006.01)
*H01J 49/04* (2006.01)

(52) U.S. Cl.
CPC ............ *G01N 1/00* (2013.01); *H01J 49/0409* (2013.01)

(58) Field of Classification Search
CPC ...................................................... G01N 1/00
USPC ....................................................... 73/864.91
See application file for complete search history.

(56) References Cited

U.S. PATENT DOCUMENTS

| | | | |
|---|---|---|---|
| 5,571,410 | A  | 11/1996 | Swedberg |
| 6,361,745 | B1 | 3/2002  | Regan |
| 6,395,554 | B1 | 5/2002  | Regan |
| 6,485,918 | B1 | 11/2002 | Schermer |
| 6,825,478 | B1 | 11/2004 | McCarthy |
| 7,361,208 | B2 | 4/2008  | Botelho |
| 7,671,345 | B2 | 3/2010  | Blackmore |
| 2003/0044837 | A1 | 3/2003 | Schermer |
| 2004/0110275 | A1 | 6/2004 | Sandell |
| 2005/0116163 | A1 | 6/2005 | Park |
| 2005/0133714 | A1 | 6/2005 | Vestal |
| 2005/0161598 | A1 | 7/2005 | Guevremont |
| 2005/0247701 | A1 | 11/2005 | Deka |
| 2005/0258088 | A1 | 11/2005 | Botelho |
| 2006/0207115 | A1 | 9/2006 | Truche |
| 2007/0228271 | A1 | 10/2007 | Truche |
| 2008/0047323 | A1 | 2/2008 | Botelho |
| 2008/0105033 | A1 | 5/2008 | Tipler |
| 2008/0272286 | A1 | 11/2008 | Vestal |
| 2009/0032695 | A1 | 2/2009 | Kaye |

(Continued)

FOREIGN PATENT DOCUMENTS

WO    2010144859    12/2010

OTHER PUBLICATIONS

U.S. Appl. No. 13/662,745, filed Oct. 29, 2012, Paul St. Cyr et al.

(Continued)

*Primary Examiner* — Michael A Lyons
*Assistant Examiner* — Alexander Mercado
(74) *Attorney, Agent, or Firm* — Rhodes IP PLC; Christopher R Rhodes

(57) ABSTRACT

Certain embodiments described herein are directed to sample platforms that are configured to permit electrical coupling between a sample support and electrical ground. In some examples, a sample platform configured to receive a sample support effective to retain a sample for direct sample analysis and comprising an aperture for receiving at least one electrical coupler configured to engage the sample support and provide electrical coupling between the sample support and ground is described.

20 Claims, 15 Drawing Sheets

(56) References Cited

U.S. PATENT DOCUMENTS

| | | |
|---|---|---|
| 2010/0059674 A1 | 3/2010 | Chen |
| 2010/0102248 A1 | 4/2010 | Milas |
| 2010/0136699 A1 | 6/2010 | Drese |
| 2011/0032611 A1 | 2/2011 | Mick |
| 2011/0122396 A1 | 5/2011 | Ivaldi |
| 2012/0285325 A1 | 11/2012 | Tipler |
| 2012/0312980 A1 | 12/2012 | Whitehouse |

OTHER PUBLICATIONS

U.S. Appl. No. 13/662,500, filed Oct. 28, 2012, Paul St. Cyr et al.
U.S. Appl. No. 13/487,037, filed Jun. 1, 2012, Whitehouse.
IPRP for PCT/US2013/066994 dated Mar. 27, 2014.
PerkinElmer's AxION Direct Sample Analysis System (retrieved online Mar. 7, 2014 from https:www.youtube.com/watch?v=ZTxr9gCU_Qw>).
IPRP for PCT/US2013/066995 dated Mar. 27, 2014.
Supplementary European Search Report and Written Opinion for EP13849644.3.

SAMPLE PLATFORMS AND METHODS OF USING THEM

TECHNOLOGICAL FIELD

Certain features, aspects and embodiments are directed to sample platforms and methods of using them. In certain examples, the sample platform can be configured to permit electrical coupling of a sample support on the sample platform to electrical ground.

BACKGROUND

Direct sample analysis permits analysis of a sample by directly introducing the sample into an instrument. If desired, front-end chromatography separation can be omitted prior to analysis of the sample.

SUMMARY

Certain features, aspects and embodiments described herein are directed to sample platforms and sample holder assemblies that can be used to retain a sample support on the sample platform to permit direct sample analysis. The exact configuration of the sample platforms and sample holder assemblies may vary, and illustrations of different types of sample holders are described in detail below.

In one aspect, a sample holder assembly for use in direct sample analysis is provided. In certain embodiments, the sample holder assembly comprises a sample platform configured to retain a sample support effective to retain a sample for direct sample analysis, the sample platform comprising at least one aperture. In some examples, the sample holder assembly also comprises an electrical coupler configured to couple to the sample support and the sample platform through the at least one aperture of the sample platform to retain the sample support on the sample platform and provide electrical coupling of the sample support to ground.

In certain embodiments, the electrical coupler is configured to engage an alignment coupler, the alignment coupler configured to electrically couple the sample support to the ground and to align the sample support on the sample platform for analysis. In other embodiments, the electrical coupler engages the alignment coupler through a friction fit. In further embodiments, the alignment coupler comprises threads configured to couple to threads of the at least one aperture. In additional embodiments, the assembly can comprise a second aperture on the sample platform, in which the second aperture is configured to electrically couple the sample support to the ground through an additional electrical coupler. In some examples, the sample holder assembly further comprises a first alignment coupler and a second alignment coupler, in which the first alignment coupler is configured to engage the electrical coupler and the second alignment coupler is configured to engage the additional electrical coupler to provide electrical coupling of the sample support to ground. In additional examples, the sample holder assembly comprises an orientation contact on the sample platform, the orientation contact configured to permit coupling of the sample support to the sample platform in a single orientation. In some embodiments, the sample holder assembly comprises an actuation contact on the sample platform that is configured to engage a sealing device. In other embodiments, the actuation contact on the sample platform is configured to permit rotation of the sealing device up to about 180 degrees. In certain examples, the electrical coupler is configured to provide the electrical coupling between the sample support and the ground without the use of any threaded fasteners.

In an additional aspect, a sample holder assembly comprising a sample platform comprising an electrical coupler configured to electrically couple a sample support to ground through an electrically conductive locating pin on the sample support, and an additional electrical coupler configured to couple to the electrical coupler of the sample platform and the electrical coupler of the sample support to provide electrical coupling between the sample support and the ground is described.

In certain embodiments, the sample holder assembly comprises a second electrical coupler on the sample platform that is configured to couple to a second electrically conductive locating pin on the sample support to electrically couple the sample support to the ground. In other embodiments, the sample holder assembly comprises a first adapter configured to couple to the electrical coupler and the first locating pin and a second adapter configured to couple to the second electrical coupler and the second locating pin to permit coupling of the sample support to the sample platform and provide electrical coupling between the sample platform and the ground. In some examples, the electrical coupler and the second electrical coupler are polarized to permit coupling of the sample support to the sample platform in a single orientation. In other examples, the sample holder assembly comprises an orientation contact on the sample platform to permit engagement of the sample support to the sample platform in a single orientation. In further embodiments, the sample holder assembly comprises an actuation contact on the sample platform that is configured to engage a sealing device. In some embodiments, the actuation contact on the sample platform is configured to permit rotation of the sealing device up to about 180 degrees. In some embodiments, the sample support is configured to receive a sample for direct sample analysis. In other embodiments, the electrical coupler of the sample platform is configured to engage the locating pin of the sample support through a friction fit. In some examples, the electrical coupler of the sample platform is configured to provide the electrical coupling between the sample support and the ground without the use of any threaded fasteners.

In another aspect, a sample holder assembly comprising a sample platform configured to retain a sample support effective to retain a sample for direct sample analysis, the sample platform comprising at least one integral coupler configured to couple the sample platform to a sample support, an electrical coupler configured to couple to the at least one integral coupler of the sample platform and provide the electrical coupling of the sample support to ground, and an alignment coupler configured to engage to the electrical coupler to permit the electrical coupling of the sample support to the ground and to align the sample support on the sample platform. In some embodiments, the integral electrical coupler comprises stainless steel. In other embodiments, the sample platform further comprises a second integral coupler configured to couple the sample support to the sample platform. In some examples, the integral coupler and the second integral coupler are sized differently. In further examples, the integral coupler and the second integral coupler are substantially parallel to each other. In certain examples, the sample holder assembly comprises a second electrical coupler configured to couple to the second integral coupler to provide electrical coupling of the sample support to the ground. In additional examples, the integral coupler and the second integral coupler are sized substantially the same and the electrical coupler and the second electrical coupler are sized differently. In some embodiments, the sample holder assembly comprises a second alignment coupler configured to couple to the second electrical coupler to provide the electrical coupling of the second electrical coupler to the ground. In certain examples, the electrical coupler and the second electrical coupler are sized substantially the same and the alignment coupler and the second alignment coupler are sized differently. In other examples, the integral coupler and the second integral coupler are sized substantially the same, the electrical coupler and the second electrical coupler are sized differently and in which the alignment coupler is sized to engage to the electrical coupler and the second alignment coupler is sized to engage to the second electrical coupler to permit insertion of the sample holder into the sample support in a single orientation.

In an additional aspect, a sample holder assembly comprising a sample support comprising a first coupler, and a sample platform comprising a first aperture configured to reversibly couple to the first coupler of the sample support, the aperture of the sample platform configured to align the sample support on the sample platform and provide electrical coupling of the sample support to ground is disclosed.

In certain examples, the sample support further comprises a second coupler configured to electrically couple the sample support to ground, and in which the sample platform comprises a second aperture configured to reversibly couple to the second coupler to provide electrical coupling of the sample support to the ground. In other examples, the first aperture and the second aperture are sized and arranged to permit insertion of the sample support into the sample platform in a single orientation. In some examples, the sample platform comprises a removable alignment coupler configured to permit coupling of the sample support into the sample platform in a single orientation. In certain embodiments, the sample holder assembly further comprises an electrical coupler configured to electrically couple to the first coupler and the first aperture to permit electrical coupling of the sample support to the ground. In other embodiments, the sample support further comprises a second coupler configured to electrically couple the sample support to ground, and in which the sample platform comprises a second aperture configured to reversibly couple to the second coupler of the sample support to permit electrical coupling of the sample support to the ground, the sample holder assembly further comprising a first electrical coupler configured to electrically couple to the first coupler of the sample support and the first aperture of the sample platform to permit electrical coupling of the sample support to the ground and a second electrical coupler configured to electrically couple to the second coupler of the sample support and the second aperture of the sample platform to permit electrical coupling of the sample support to the ground. In additional embodiments, the first electrical coupler and the second electrical coupler are sized and arranged to permit coupling of the sample support to the first and second apertures, respectively, of the sample platform in a single orientation. In some examples, the sample platform comprises an alignment coupler configured to permit coupling of the sample support to the sample platform in a single orientation. In other examples, the sample holder assembly comprises a first alignment coupler configured to couple to the first aperture of the sample platform and the first electrical coupler to permit electrical coupling of the sample support to the ground. In some embodiments, the sample holder assembly comprises a second alignment coupler configured to couple to the second aperture of the sample platform and the second electrical coupler to permit electrical coupling of the sample support to the ground.

In another aspect, a sample holder assembly comprising a sample support comprising a first coupler configured to couple the sample support to a sample platform, a first electrical coupler configured to couple to the first coupler of the sample support, and a first alignment coupler configured to couple to the first electrical coupler and to the sample support to provide electrical coupling between the sample support and the ground is provided.

In certain embodiments, the sample support is configured to retain a sample support configured for direct sample analysis. In other embodiments, the sample support further comprises a second coupler configured to couple to the sample platform, and the sample holder assembly comprises a second electrical coupler configured to couple to the second coupler of the sample support. In some embodiments, the sample holder assembly further comprises a second alignment coupler configured to couple to the second electrical coupler to provide electrical coupling between the sample support and the ground. In further embodiments, the sample holder assembly further comprises a sample platform comprising a first aperture configured to couple to the first coupler of the sample support. In additional embodiments, the sample holder support comprises an orientation contact configured to permit coupling of the sample support to the sample platform in a single orientation. In some examples, the sample holder assembly further comprises an actuation contact on the sample platform that is configured to engage a sealing device. In certain examples, the actuation contact on the sample platform is configured to permit rotation of the sealing device up to about 180 degrees. In other examples, the sealing device is configured as a cover. In some embodiments, the cover comprises a cam configured to slidingly engage the actuation contact of the sample platform support to rotate the door and permit loading of a sample into the sample support.

In an additional aspect, a sample holder assembly configured to receive a sample holder for direct sample analysis, the sample holder assembly comprising a sample support effective to retain a sample for direct sample analysis, the sample support comprising a first coupler and a second coupler each configured to electrically couple the sample support to ground, and a sample platform comprising a first aperture configured to couple to the first coupler of the sample support and a second aperture configured to couple to the second coupler of the sample support, the sample platform comprising an actuation contact that is configured to engage a sealing device is described.

In certain embodiments, the assembly further comprise a first electrical coupler configured to couple to the first coupler, and a second electrical coupler configured to couple to the second coupler, the first and second electrical couplers configured to provide electrical coupling between the sample support and the ground. In some instances, the first and second apertures of the sample platform are sized differently to permit coupling of the sample support to the sample platform in a single orientation. In other configurations, the assembly comprises a first insert configured to couple to the first aperture and the first electrical coupler, and a second insert configured to couple to the second aperture and the second electrical coupler. In additional examples, the first and second electrical couplers are sized differently and the first and second inserts are sized differently to permit coupling of the sample support to the sample platform in a single orientation. In some examples, the actuation contact is configured to engage a cam of the sealing device to permit rotation of the sealing device up to about 180 degrees. In other examples, the sealing device comprises a cover. In some examples, the assembly further comprises an orientation contact on the sample platform, the orientation contact configured to permit coupling of the sample support to the sample platform in a single orientation. In certain embodiments, the first coupler and the first aperture are sized similarly and the second coupler and the second aperture are sized similarly and different from the sizing of the first coupler and the first aperture to permit coupling of the sample support to the sample platform in a single orientation. In other embodiments, the first coupler and the second coupler couple to the first aperture and the second aperture, respectively, through a friction fit.

In another aspect, a sample platform configured to receive a sample support effective to retain a sample for direct sample analysis, the sample platform comprising at least one electrical coupler configured to engage the sample support and provide electrical coupling between the sample support and ground is disclosed. In certain examples, the electrical coupler of the sample platform is configured to engage an electrical coupler on the sample support to provide the electrical coupling between the sample support and the ground. In other examples, the sample platform comprises an additional electrical coupler, and in which the electrical coupler of the sample platform is configured to engage a first electrical coupler on the sample support, and the additional electrical coupler of the sample platform is configured to engage a second electrical coupler on the sample support to provide the electrical coupling between the sample support and the ground. In some embodiments, the platform comprises an orientation contact configured to permit coupling of the sample support to the sample platform in a single orientation. In certain examples, the platform comprises an actuation contact on the sample platform that is configured to engage a sealing device. In some examples, the actuation contact is configured to permit rotation of the sealing device up to about 180 degrees. In other examples, the electrical coupler is configured to releasably engage the sample support through a friction fit. In further examples, the electrical coupler is configured to releasably engage the sample support through an electrical coupler of the sample support. In certain embodiments, the electrical coupler comprises threads to engage the sample platform, and the sample support comprises an electrical coupler that is configured to engage the electrical coupler of the sample platform through a friction fit. In some embodiments, the electrical coupler is sized and arranged to receive at least one locating pin of the sample support to provide electrical coupling between the sample support and ground.

In an additional aspect, a sample platform configured to receive a sample support effective to retain a sample for direct sample analysis, the sample platform comprising at least one aperture configured to receive an electrical coupler of a sample support to permit electrical coupling between the sample support and ground is disclosed. In certain examples, the electrical coupler of the sample support is configured as a pin that couples to the at least one aperture of the sample platform. In other embodiments, the at least aperture of the sample platform is electrically conductive. In some examples, the at least one aperture is sized and arranged to receive an electrical coupler configured to couple to the electrical coupler of the sample support to provide electrical coupling between the sample support and the ground. In certain examples, the platform comprises an additional aperture configured to receive an additional electrical coupler of a sample support to permit electrical coupling between the sample support and the ground. In other examples, the electrical coupler of the sample support and the additional electrical coupler of the sample support are each configured as a pin that couples to the at least one aperture and the additional aperture, respectively, of the sample support. In some examples, the at least one aperture is sized and arranged to receive the electrical coupler of the sample support to electrically couple the electrical coupler of the sample support to ground and in which the additional aperture is sized and arranged to receive the additional electrical coupler of the sample support to electrically couple the additional electrical coupler of the sample support to ground. In some embodiments, the platform comprises an orientation contact configured to permit coupling of the sample support to the sample platform in a single orientation. In some examples, the platform comprises an actuation contact on the sample platform that is configured to engage a sealing device. In some embodiments, the actuation contact is configured to permit rotation of the sealing device up to about 180 degrees.

In another aspect, a kit comprising a sample platform configured to retain a sample support effective to retain a sample for direct sample analysis, the sample platform comprising a first integral coupler configured to couple the sample platform to the sample support to provide electrical coupling between the sample holder and ground is provided. In some examples, the kit comprises a first electrical coupler configured to couple to the first coupler of the sample platform to provide the electrical coupling between the sample support and the ground. In other examples, the sample platform of the kit comprises a second coupler configured to provide electrical coupling between the sample support and the ground. In some examples, the kit comprises a first electrical coupler configured to couple to the first coupler of the sample platform, and a second electrical coupler configured to couple to the second coupler of the sample platform, each of the first and second electrical couplers configured to permit electrical coupling between the sample support and the ground. In additional examples, the kit comprises an insert configured to couple to at least one of the first electrical coupler and the second electrical coupler. In some embodiments, the sample platform of the kit comprises a first aperture configured to couple to the first electrical coupler and a second aperture configured to couple to the second electrical coupler. In other examples, the kit comprises a first insert configured to couple to the first aperture and the first electrical coupler. In further examples, the kit comprises a second insert configured to couple to the second aperture and the second electrical coupler. In some embodiments, the first insert and the second insert are sized differently to permit coupling of the sample support to the sample platform in a single orientation. In additional embodiments, the sample platform further comprises an actuation contact configured to engage a sealing device.

In another aspect, a method of analyzing a sample using direct sample analysis is provided. In certain examples, the method comprises providing a sample platform comprising a first integral coupler configured to provide electrical coupling between a sample support coupled to the sample platform and ground. In certain embodiments, the method comprises providing a first electrical coupler configured to couple to the first integral coupler and permit electrical coupling between the sample support and the ground. In certain examples, the method comprises providing the sample platform with a second integral coupler configured to provide electrical coupling between the sample support and ground. In some embodiments, the method comprises providing a first electrical coupler configured to couple to the first integral coupler and a second electrical coupler configured to couple to the second integral coupler, each of the first and second electrical coupler configured to permit electrical coupling between the sample support and the ground. In other embodiments, the method comprises providing an insert configured to couple to at least one of the first electrical coupler and the second electrical coupler. In some examples, the method comprises providing the sample platform comprising a first aperture configured to couple to the first electrical coupler and a second aperture configured to couple to the second electrical coupler. In other examples, the method comprises providing a first insert configured to couple to the first aperture and the first electrical coupler. In certain examples, the method comprises providing a second insert configured to couple to the second aperture and the second electrical coupler. In other examples, the method comprises providing a first insert and a second insert sized differently than the first insert to permit coupling of the sample support to the sample platform in a single orientation. In additional examples, the provided sample platform further comprises an actuation contact configured to engage a sealing device.

In an additional aspect, a method of electrically grounding a sample support configured to retain a sample for direct sample analysis is disclosed. In certain embodiments, the method comprises providing a sample support with at least one coupler configured to reversibly couple the sample support to a sample platform to provide electrical coupling of the sample support to ground.

In some examples, the method comprises providing the ground to the sample support without using any threaded fasteners to couple the sample support to the sample platform. In certain embodiments, the method comprises providing a sample platform comprising an aperture configured to couple to the at least one coupler of the sample support. In additional embodiments, the method comprises providing at least one electrical insert configured to couple to the at least one coupler and the aperture of the sample platform to provide electrical coupling between the sample support and the ground. In certain examples, the method comprises configuring the sample support with at least one additional coupler configured to reversibly couple the sample support to a sample platform and provide the electrical coupling between the sample support and the ground. In some examples, the method comprises providing a first electrical insert and a second electrical insert each configured to couple to one of the least one coupler and the additional coupler. In certain embodiments, the method comprises providing a sample platform comprising a first aperture configured to couple to the at least one coupler of the sample support and a second aperture configured to couple to the additional coupler of the sample support. In other embodiments, the method comprises configuring the sample platform with an orientation contact to permit coupling of the sample support to the sample platform in a single orientation. In certain examples, the method comprises configuring the sample platform with an actuation contact that is configured to engage a sealing device. In further embodiments, the actuation contact is configured to permit rotation of the sealing device up to about 180 degrees.

Other aspects and attributes will become apparent to those skilled in the art after review of the detailed description and accompanying drawings.

BRIEF DESCRIPTION OF FIGURES

Certain configurations are provided below for illustrative purposes only with reference to the accompanying figures in which.

Additional features, aspects and embodiments are described in more detail below. It will be recognized by the person of ordinary skill in the art, given the benefit of this disclosure, that the lengths and dimensions shown in the figures are not limiting and that many different lengths and dimensions can be used depending on the size of the sample support, the system which the sample platform is to be used in and other factors.

DETAILED DESCRIPTION

Certain embodiments of sample platforms and sample holder assemblies including them are described in detail below. The exact configuration of the sample platforms including, for example, the length and width of the platforms, size and configuration of the apertures that can receive electrical couplers, materials used in the platforms and the like can vary depending on the particular instrument the sample platform is to be used in and/or depending on the nature of the sample to be analyzed. Where direct sample analysis is referred to below, no particular configuration of a direct sample analysis device or system is intended to be required as being necessary for properly using the sample platform. For illustration purposes, some configurations of a direct sample analysis device or system are described herein. The term "platform" is used for convenience purposes to refer to a generally planar structure that can include suitable features or components to permit coupling of a sample support. The term sample support refers to a holder, device or other structure that is effective to retain a sample, for at least some period, to permit analysis of the sample. In some instances, the sample support may be configured to receive a mesh, screen or other material that is effective to receive and retain a sample for analysis. Certain examples of the sample platforms described herein refer to apertures or openings. While some illustrations show one or two apertures being present, more than two apertures may be present if desired. In addition, where more than a single aperture is present, the size and/or configuration of the apertures may be different or substantially the same.

Figure 1:
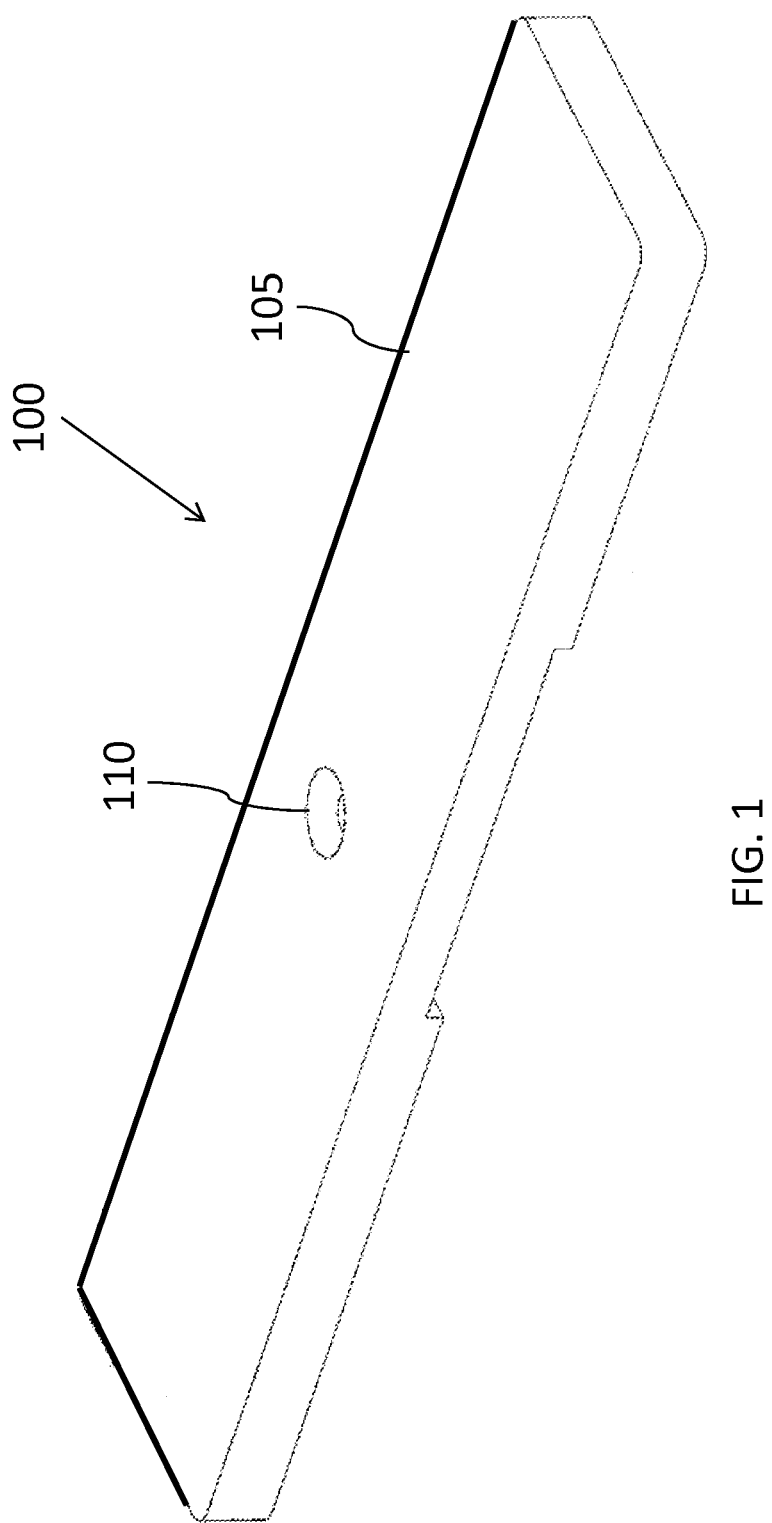
FIG. 1 is an illustration of a sample platform comprising a single aperture, in accordance with certain examples.
Figure 2:
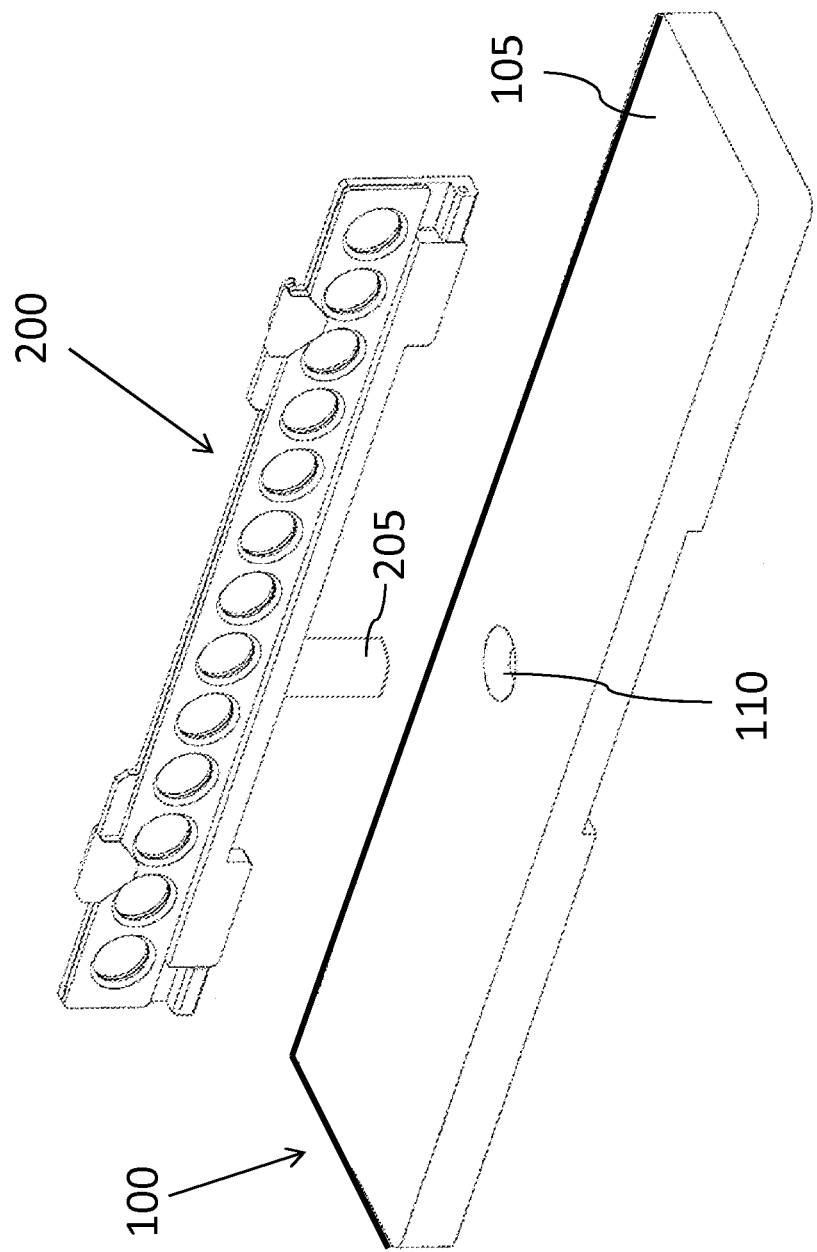
FIG. 2 is an illustration of a sample support comprising a coupler configured to couple to the sample platform of FIG. 1, in accordance with certain examples.

In certain embodiments, a sample platform configured to receive a sample support effective to retain a sample for direct sample analysis is shown in FIG. 1. The platform 100 comprises a generally planar surface 105 with at least one aperture 110. The aperture 110 may take many different forms and shapes including circular, square, rectangular or other geometric shapes. The surface 105 may be produced using any of the illustrative materials described herein. In some embodiments, the aperture can be configured to receive a coupler, e.g., an electrical coupler, of a sample support to permit electrical coupling between the sample support and ground. Referring to FIG. 2, a sample support 200 is shown that includes a coupler 205, e.g., an electrical coupler, that can be engaged, inserted or otherwise coupled to the aperture 110 to provide electrical coupling between the sample support 200 and an electrical ground. Without wishing to be bound by any particular scientific theory, the sample support 200 may be subjected to a beam or fluid of charged particles to ionize sample retained by the sample support 200. Charge can build up on the surfaces of the sample support 200 and can effect ionization of sample or otherwise interfere with the analysis. By electrically coupling the sample support 200 to ground, any unwanted charge build up may be reduced or avoided. If desired, the entire platform 100 may also be electrically coupled to ground and coupling of the support 200 to the platform 100 acts to ground the sample support 200.

In some embodiments, the coupler 205 of the sample support 200 can be configured as a pin that couples to the aperture 110 of the sample platform 100. The pin can be sized and arranged to provide a friction fit with the aperture 110 such that coupling of the pin to the aperture 110 acts to retain the sample support 200 in a suitable position for sample analysis. If desired, the aperture 110 can be electrically conductive and/or electrically coupled to ground to permit grounding of the sample support 200. While the coupler 205 is shown as being located medically on the sample support 200, it can alternatively be positioned at one end or in a position other than medially if desired.

Figure 3:
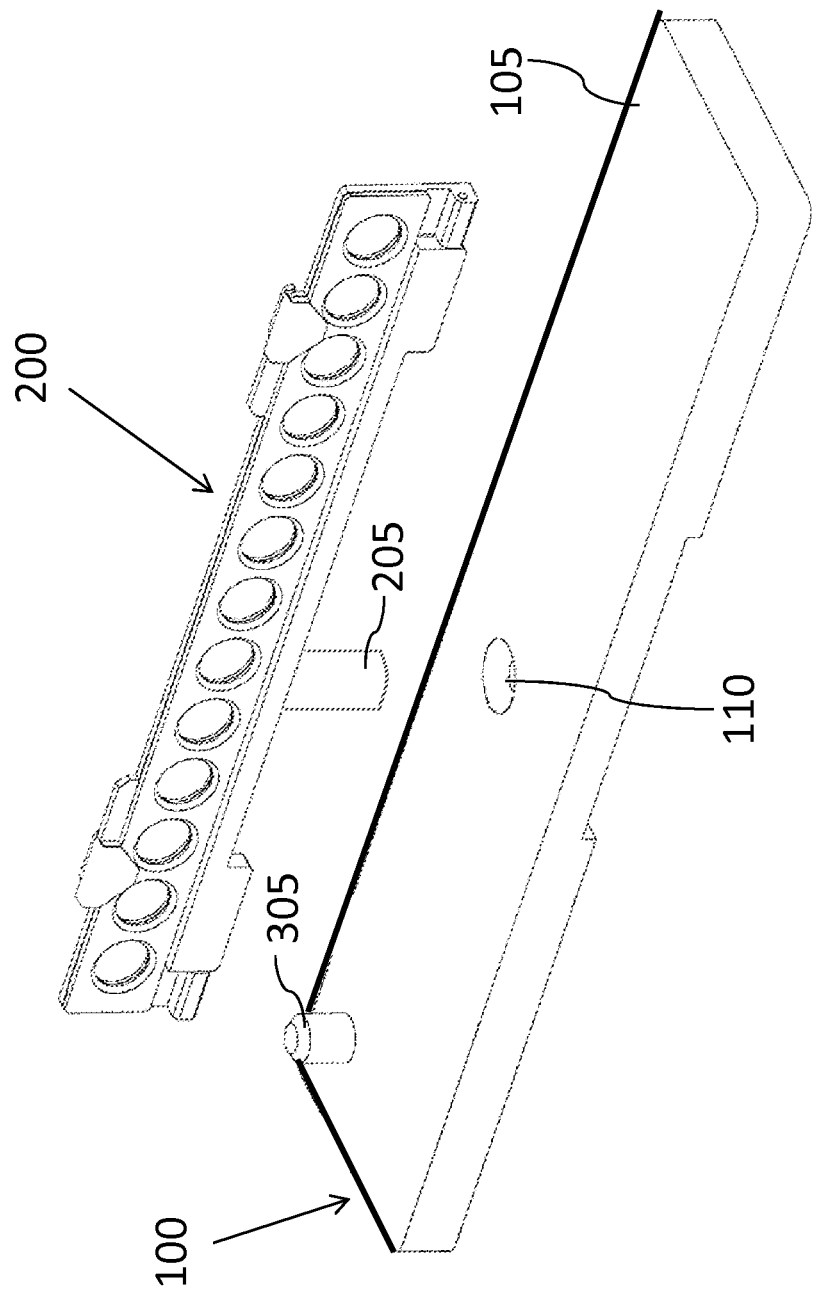
FIG. 3 is an illustration of a sample platform comprising an orientation contact, in accordance with certain examples.

In certain embodiments, the sample platform 100 can include an orientation contact or pin to prevent insertion of the sample support 200 into the aperture 110 in an incorrect orientation. For example and referring to FIG. 3, an orientation contact, shown as a pin 305, can permit coupling of the support 200 to the platform 100 in one orientation of the support 200 and generally prohibit coupling of the support 200 to the platform 100 in other orientations. The pin 305 can be effective to hit or strike a rear surface of the support 200 to position the support 200 in a proper orientation and/or angle for sampling.

Figure 4:
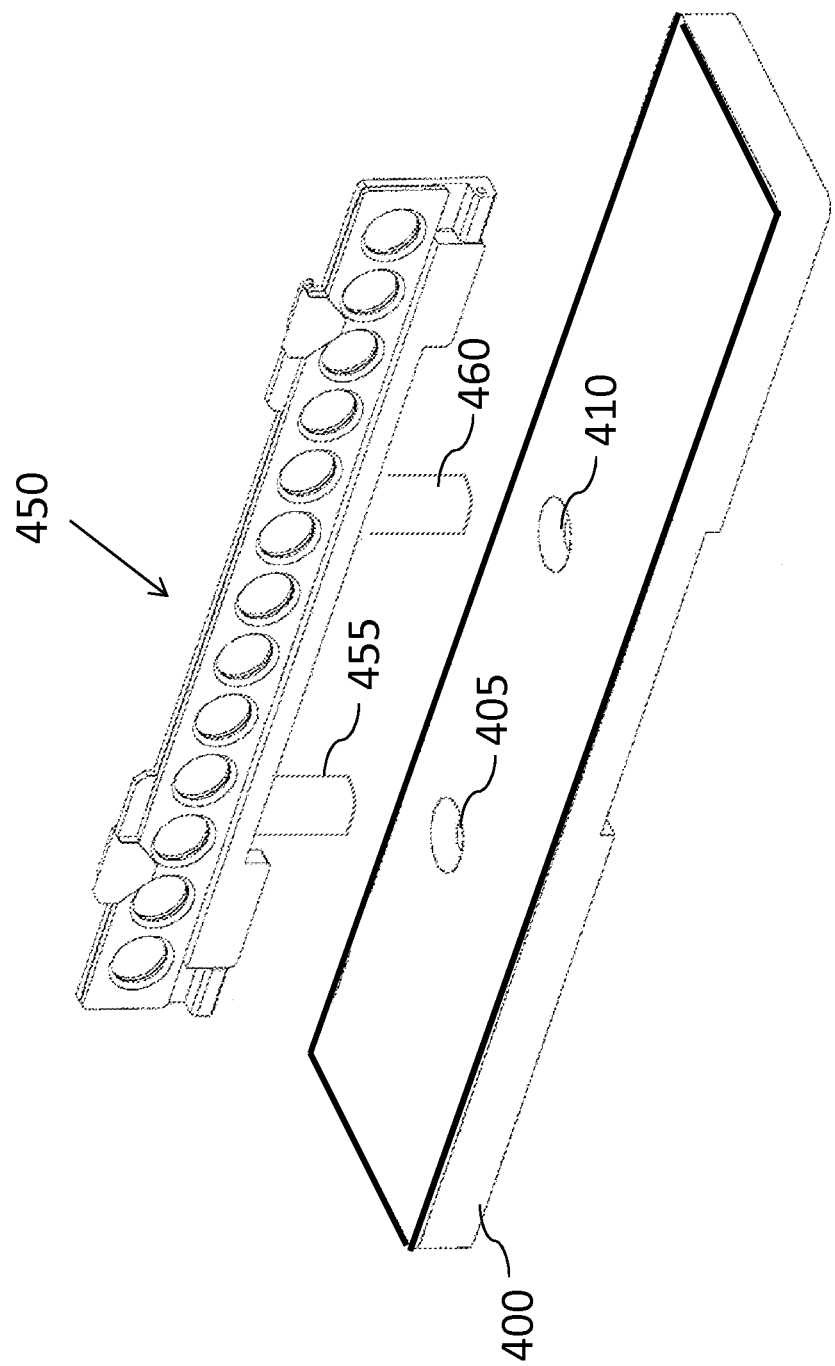
FIG. 4 is an illustration of a sample platform comprising two apertures configured to couple to two couplers on a sample support, in accordance with certain examples.

In certain embodiments, the platform can include more than a single aperture for receiving couplers of the sample support. Referring to FIG. 4, a platform 400 is shown that comprises apertures 405 and 410. Aperture 405 is sized and arranged to receive a coupler 455 on a sample support 450, and aperture 410 is sized and arranged to receive a coupler 460 on the sample support 450. In some examples, the couplers 455 and 460 can be electrically conductive to permit electrical coupling of the sample support 450 and an electrical ground. In other examples, the coupler 455 and 460 may take the form of pins that can engage the apertures 405, 410, respectively, through a friction fit to provide electrical coupling between the sample support 450 and the ground.

Figure 5:
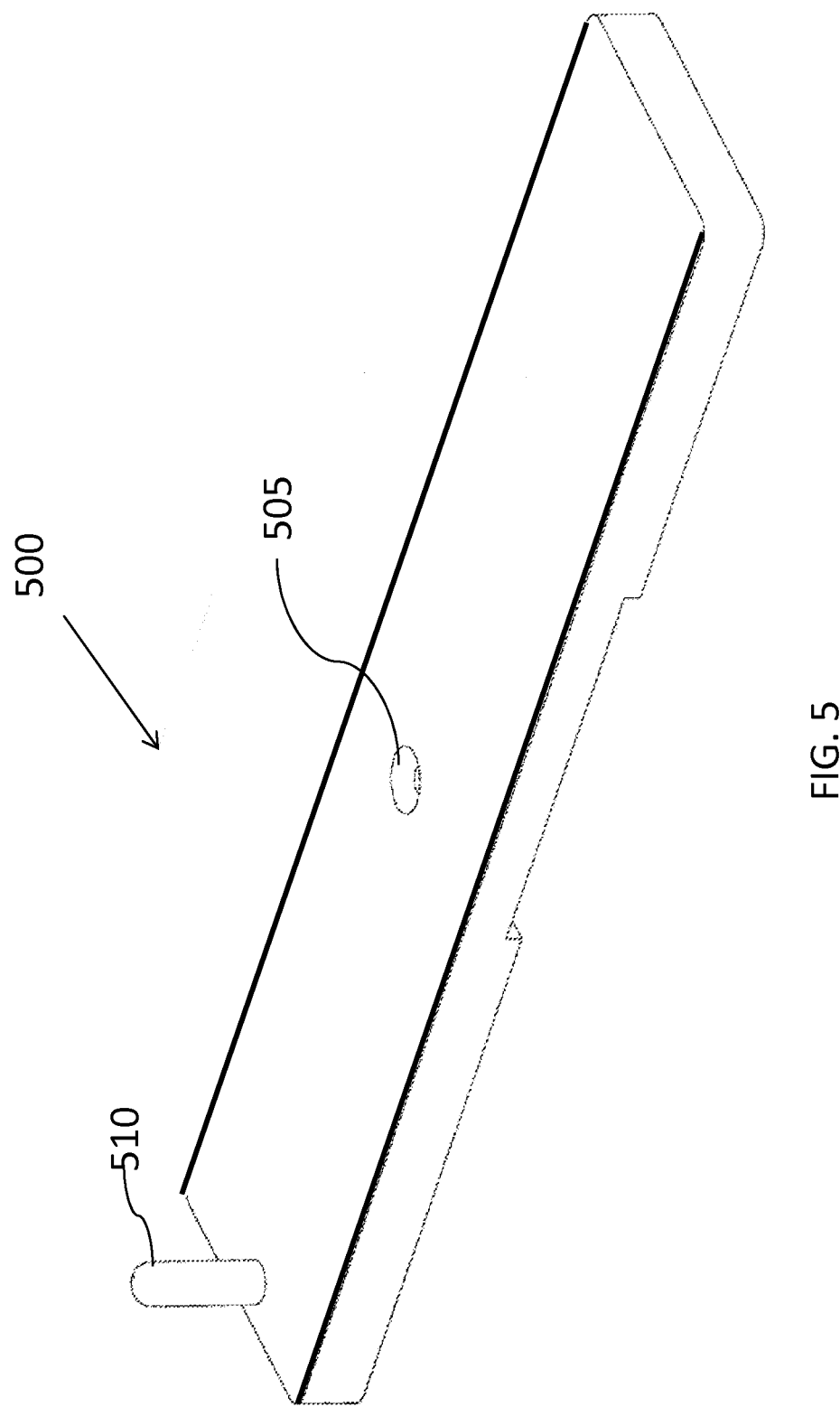
FIG. 5 is an illustration of a sample platform comprising an actuation contact, in accordance with certain examples.
Figure 6:
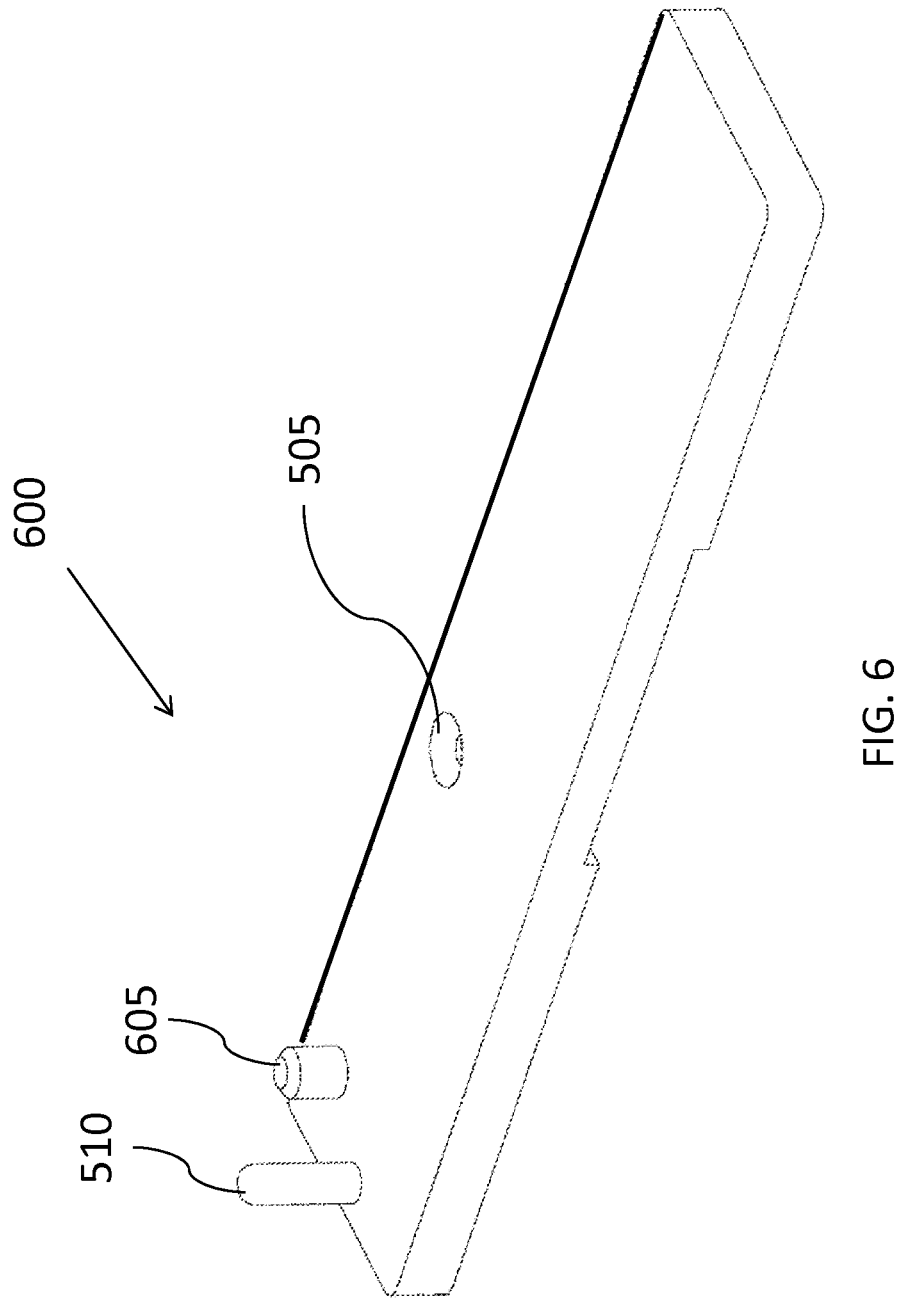
FIG. 6 is an illustration of a sample platform comprising both an actuation contact and an orientation contact, in accordance with certain examples.

In some examples, the platform can include an actuation contact that engages a sealing device that generally is effective to seal or prevent unwanted dust or air flows into the system. In some embodiments, the sealing device may provide a substantially fluid tight seal, whereas in other examples, no substantially fluid tight seal is present. Referring to FIG. 5, a platform 500 is shown that includes an aperture 505 and an actuation contact 510 at one end of the platform 500. While the actuation contact 510 is generally shown as being configured as a pin, other shapes and configurations are possible. In addition, the actuation contact may be present at other positions on the platform 500. As described in more detail below, the actuation contact 510 may permit rotation of the sealing device up to about 180 degrees. For example, the actuation contact 510 may engage a surface or cam of the sealing device as the platform 500 and sample support (not shown) is raised out of the device or system to permit loading of sample on or in the sample support. After sample is loaded, the platform 500 may be lowered, which results in disengagement of the actuation contact 510 with the sealing device and rotation of the sealing device into the closed position to generally close or cover the opening of the instrument or device where sample is loaded. If desired, the platform may also include an orientation contact 605, as shown in the platform 600 in FIG. 6, which can function similar to the orientation contact described in reference to FIG. 3.

Figure 7:
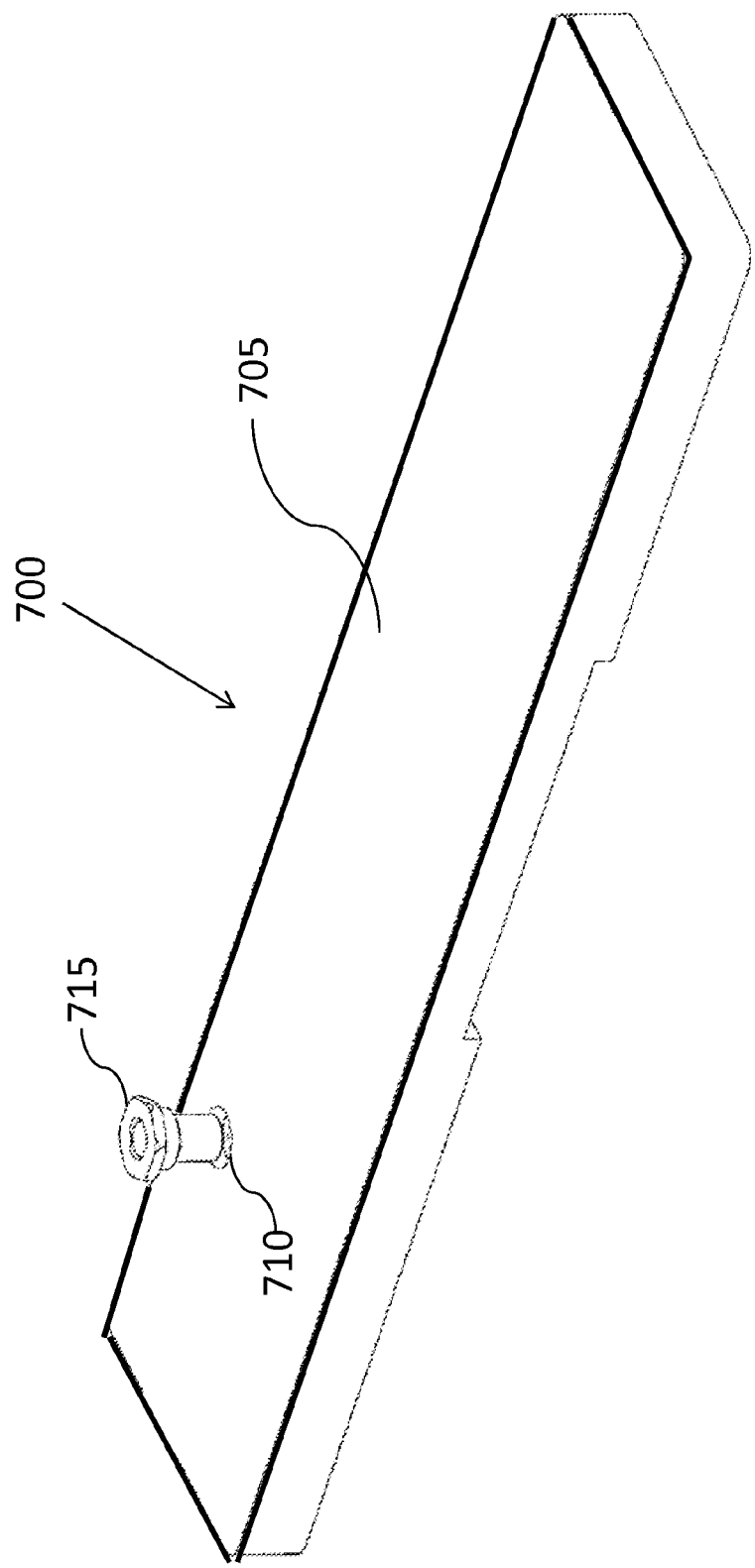
FIG. 7 is an illustration of a sample platform comprising an aperture configured to couple to an electrical coupler, in accordance with certain examples.

In certain embodiments, the sample platform can include, or can be configured to receive an electrical coupler as shown in FIG. 7. The sample platform 700 comprises a generally planar surface 705, and an aperture 710 that can receive an electrical coupler 715. If desired, the electrical coupler 715 may be integral to the platform 700 such that it is generally not removable or separable from the platform 700. In some instances, it may be desirable to use a removable electrical coupler to permit removal and cleaning of the couplers to avoid contamination of any samples. For example, where the electrical coupler 715 engages the aperture 710 through a friction fit, it may be lifted upward and removed and then cleaned using solvents, sonication or other suitable physical or chemical means. Where the electrical coupler 715 engages the aperture 710 through threads on each of the aperture 710 and the coupler 715, the coupler 715 can be unscrewed or otherwise disengaged from the aperture 710 and removed for cleaning.

Figure 8:
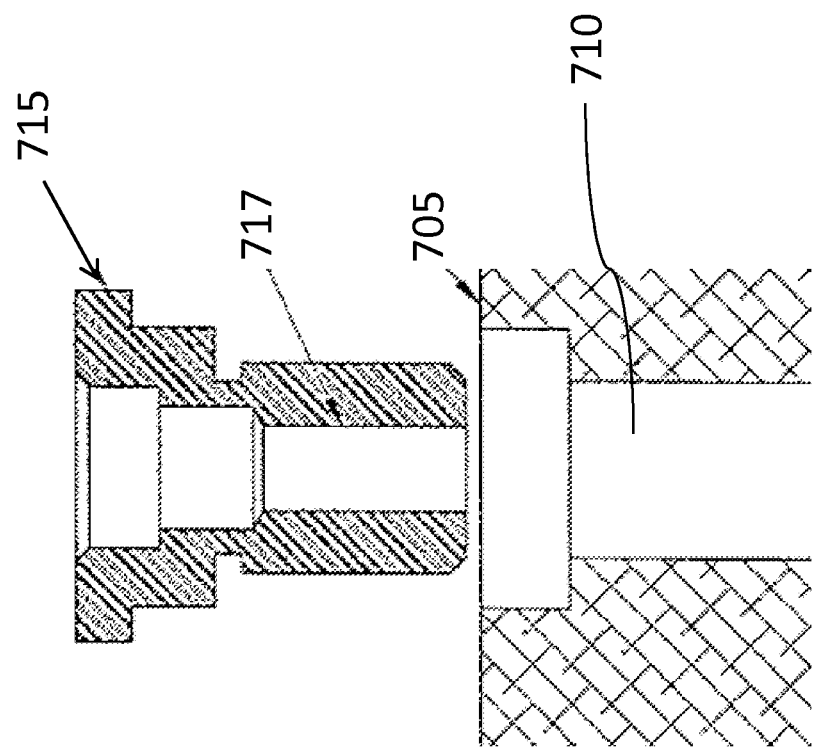
FIG. 8 is a side view of the sample platform and electrical coupler shown in FIG. 7, in accordance with certain examples.

In certain examples, a side view of the configuration shown in FIG. 7 is shown in FIG. 8. The aperture 710 may comprise a channel of varying diameter to permit insertion of the coupler 715 a desired depth into the sample platform. As shown in FIG. 8, the diameter of the aperture 710 is generally larger toward the surface 705 and decreases toward an opposite, bottom surface of the sample platform. The coupler 715 may also include an internal channel 717 that can receive an insert, another electrical coupler, a locating pin of the sample support or other features as described herein. In use of the coupler 715, it can be inserted into the aperture 710 until it encounters resistance. In some embodiments, the coupler 715 can be configured so it is flush with the surface 705 when fully inserted, whereas in other examples, the coupler 715 may include a lip or ring that sits adjacent to and above the surface 705 of the sample platform.

Figure 9:
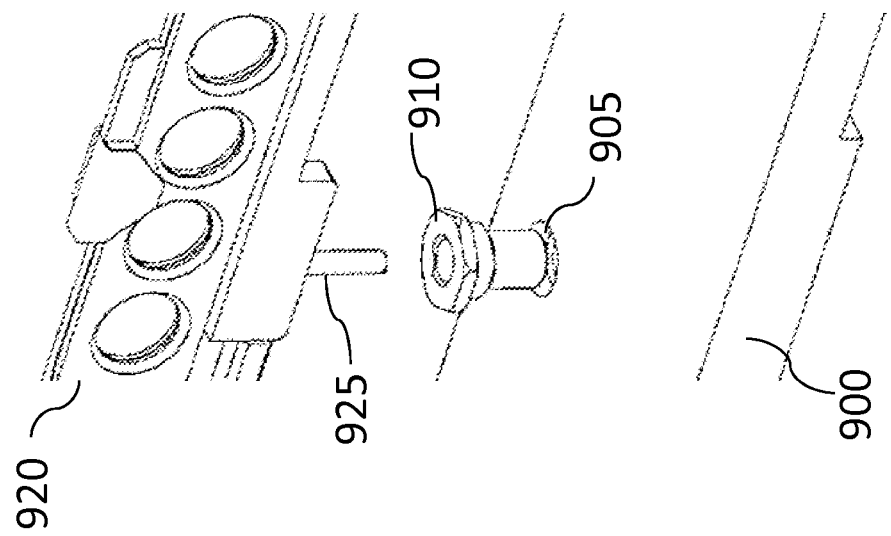
FIG. 9 is an illustration showing a sample support with a coupler configured to couple to a sample platform through an electrical coupler, in accordance with certain examples.

In certain embodiments, the coupler that engages the aperture of the sample support may be configured to couple to an electrical coupler on a sample support. Referring to FIG. 9, a sample platform 900 is shown as including an aperture 905. An electrical coupler 910 is configured to engage the aperture 915. A sample support 920 may include an electrical coupler 925, which can be configured as a locating pin, to couple the sample support to the platform 900 through the electrical coupler 910. In use, the coupler 910 can be coupled to the aperture 905. The coupler 925 of the sample support 920 is then coupled to the coupler 910 by sliding the pin 925 into the opening of the coupler 910. The coupling can align the sample support 920 at the proper angle for sampling and also permit electrical coupling of the sample support 920 to ground. In some examples, the coupler 925 couples to the coupler 910 through a friction fit. The coupler 910 may couple to the aperture 905 through a friction fit or through threads or other suitable means.

Figure 11:
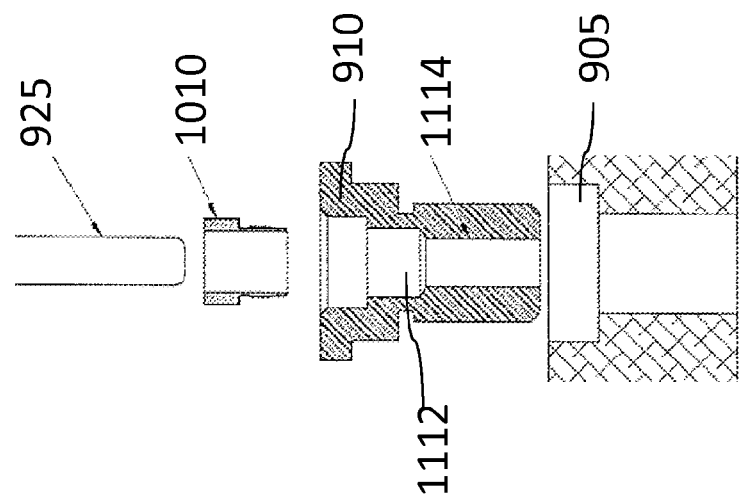
FIG. 11 is a side view of the components shown in FIG. 10, in accordance with certain examples.
Figure 10:
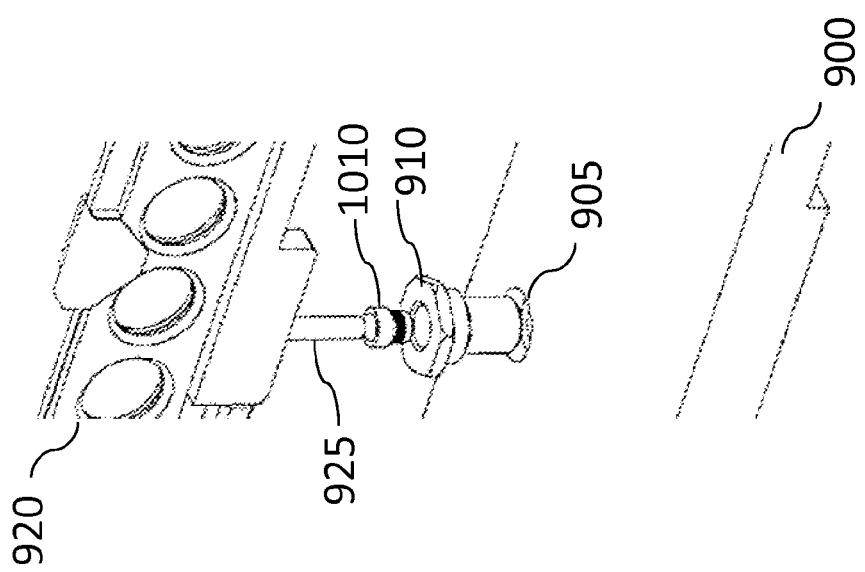
FIG. 10 is an illustration showing a sample support with a coupler configured to couple to a sample platform through an electrical coupler and an insert, in accordance with certain examples.

In some embodiments, the outer diameter of the coupler 925 may be less than the inner diameter of the coupler 910. In such instances, it may be desirable to use an insert or adapter to provide a tighter fit between the couplers 910 and 925 to permit physical contact of the components and provide the electrical coupling between them and the ground. Referring to FIG. 10, an insert 1010 is shown as being present between the couplers 910 and 925. In use, the insert 1010 can be coupled to either coupler 910 or the coupler 925. In some examples, the insert 1010 is sized and arranged to provide a tight fit between the components 910, 925 and 1010 but not so tight that removal of the sample support 920 from the sample platform 900 is difficult or requires external tools such as wrenches, pliers or pullers. The inserts 1010 can be produced from, or can include, similar materials as those of the sample support, sample platform, electrical couplers or other components of the sample holder assemblies described herein. In some embodiments, the inserts are produced using conductive, substantially inert materials such as, for example, stainless steels. Referring to FIG. 11, a side view of the insert 1010 is shown. The insert 1010 is sized and arranged to couple to an upper portion 1112 of the electrical coupler 910. The electrical coupler 910 also comprises a lower portion 1114, which is an internal diameter less than that of the internal diameter of portion 1112, and which can be coupled to the coupler 925 through the insert 1010. In certain examples, the coupler 925 is electrically coupled to the upper portion 1112 of the coupler 910 through the insert 1010 and is electrically coupled to the lower portion 1114 of the coupler 910 by physical contact with the lower portion 1114.

Figure 12:
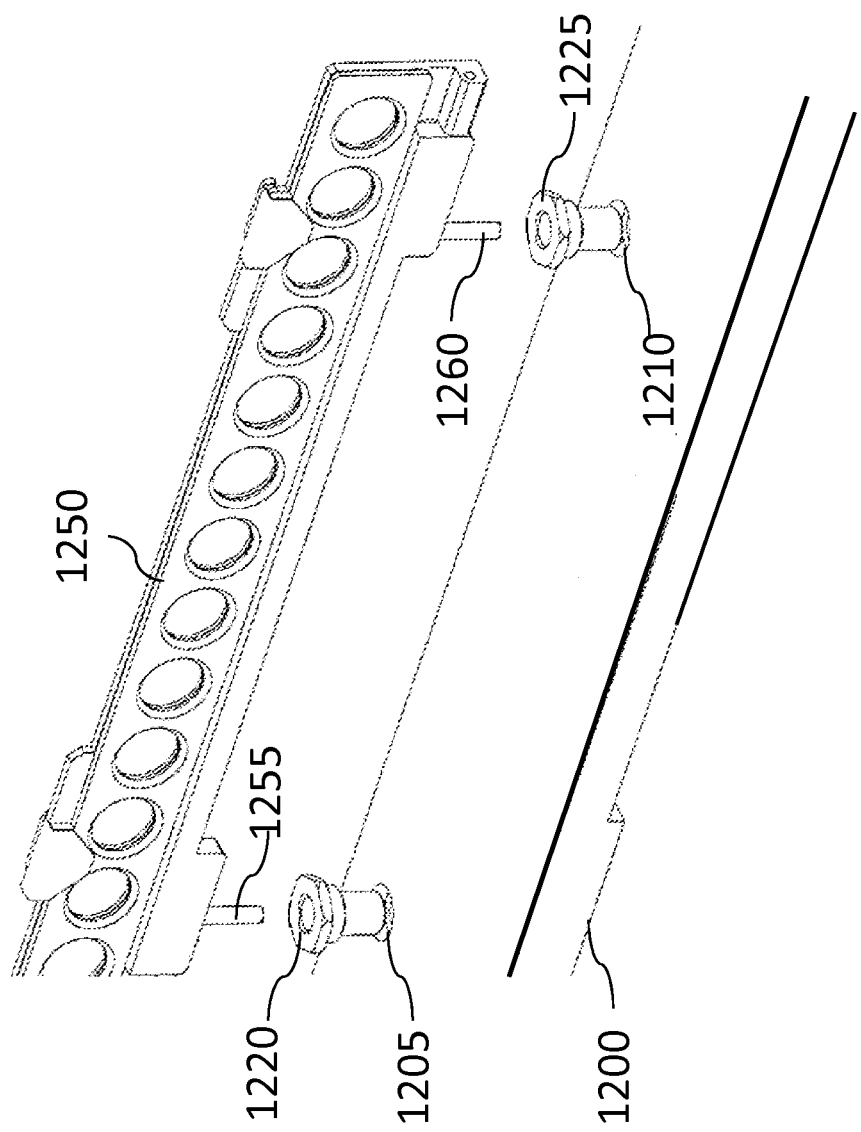
FIG. 12 is an illustration showing a sample platform comprising two apertures and a sample support configured to couple to the sample platform through two electrical couplers, in accordance with certain examples.

In certain examples, more than a single electrical coupler can be used with the sample platforms described herein. For example, where the sample platform includes two apertures, one or two electrical couplers can be used. In some examples, it may be desirable to size the apertures differently so that polarized apertures are present and the sample support can only be coupled to the sample platform in a single orientation. Referring to FIG. 12, a sample platform 1200 comprising two apertures 1205 and 1210 is shown. The aperture 1205 is sized and arranged to couple to an electrical coupler 1220, and the aperture 1210 is sized and arranged to couple to an electrical coupler 1225. A sample support 1250 comprises a first coupler 1255 and a second coupler 1260. The first coupler 1255 is configured to couple to the coupler 1220 to provide electrical coupling between the sample support 1250 and an electrical ground. The second coupler 1260 is configured to couple to the coupler 1225 to provide electrical coupling between the sample support 1250 and an electrical ground. The couplers 1255 and 1260 may engage the couplers 1220, 1225, respectively, similar to the configurations described in reference to FIGS. 8 and 9.

Figure 13:
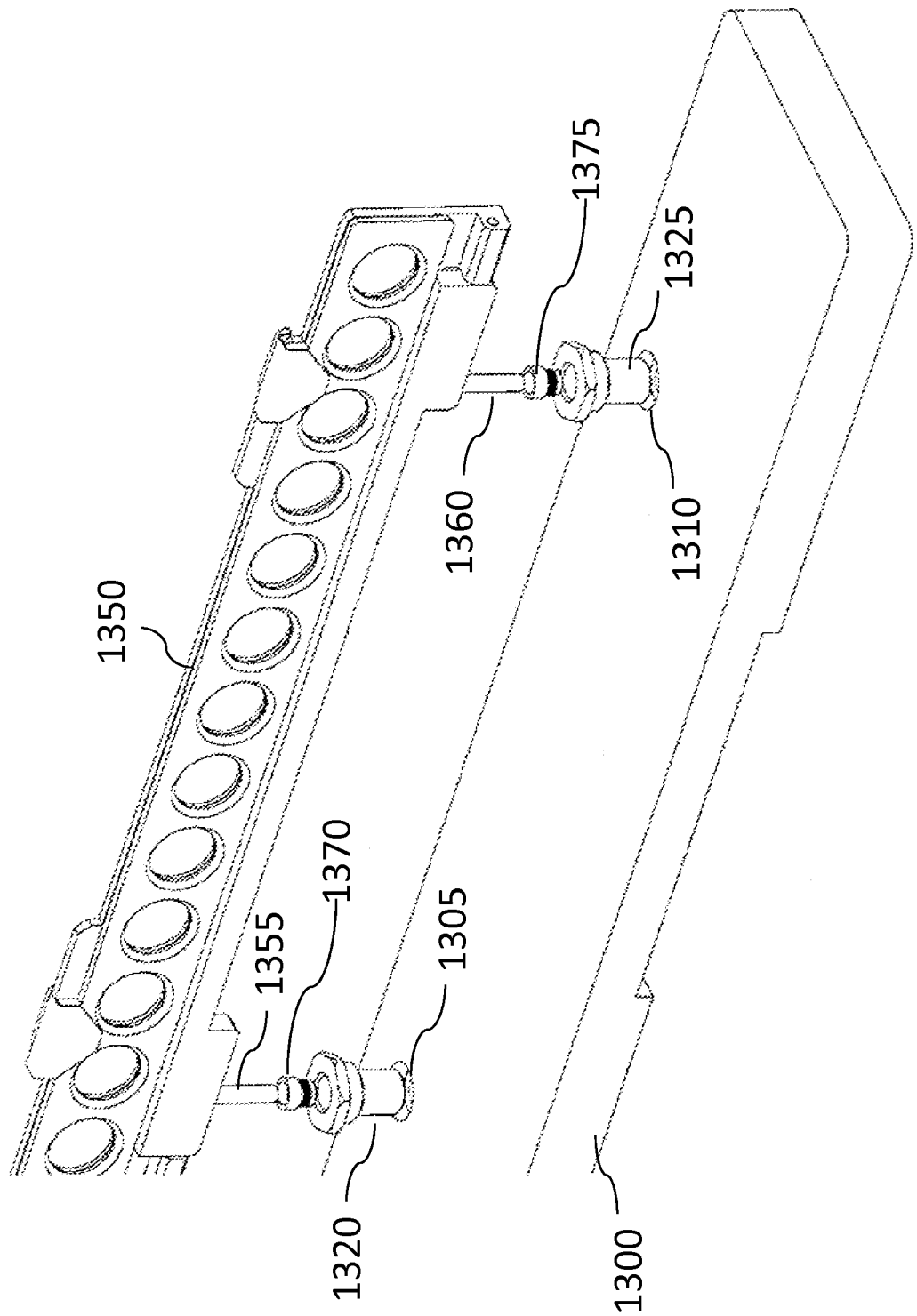
FIG. 13 is an illustration showing a sample platform comprising two apertures and a sample support configured to couple to the sample platform through two electrical couplers and two inserts, in accordance with certain examples.

In some embodiments where multiple electrical couplers are present, it may also be desirable to use multiple inserts or adapters. Referring to FIG. 13, a sample holder assembly is shown comprising a sample platform 1300 comprising two apertures 1305 and 1310. The aperture 1305 is sized and arranged to couple to an electrical coupler 1320, and the aperture 1310 is sized and arranged to couple to an electrical coupler 1325. A sample support 1350 comprises a first coupler 1355 and a second coupler 1360. The first coupler 1355 is configured to couple to the coupler 1320 to provide electrical coupling between the sample support 1350 and an electrical ground. The second coupler 1360 is configured to couple to the coupler 1325 to provide electrical coupling between the sample support 1320 and an electrical ground. The coupler 1355 couples to the coupler 1350 through an insert 1370, and the coupler 1360 coupled to the coupler 1325 through an insert 1375. Each of the inserts 1370, 1375 may be sized to engage the other couplers as shown in FIG. 11 or may take other configurations that can provide electrical coupling of the sample support 1350 to an electrical ground.

In certain embodiments, the sample platforms shown in FIGS. 12 and 13 may also include orientation contacts, actuation contacts and other features. For example, the sample platforms 1200 and 1300 can each include an orientation contact configured to permit coupling of the sample support to the sample platform in a single orientation. In some examples, the sample platforms 1200 and 1300 can include an actuation contact on the sample platform that is configured to engage a sealing device. In some embodiments, the actuation contact can be configured to permit rotation of the sealing device up to about 180 degrees.

In certain embodiments, various combinations of the features described in reference to FIGS. 1-13 may be used to provide a sample holder assembly for use in direct sample analysis. In some embodiments, the sample holder assembly can include a sample platform configured to retain a sample support effective to retain a sample for direct sample analysis, the sample platform comprising at least one aperture, and an electrical coupler configured to couple to the sample support and the sample platform through the at least one aperture of the sample platform to retain the sample support on the sample platform and provide electrical coupling of the sample support to ground. In some instances, the sample support may include a plurality of apertures as shown in FIGS. 12 and 13 and can include a sample disposed on a material exposed through the apertures of the sample support. In some embodiments, a mesh or screen can be present at the apertures and can be impacted or receive a fluid, e.g., an ion stream, to ionize sample on the mesh or screen.

In certain examples, electrical couplers of the sample assembly can be configured to engage an alignment coupler to electrically couple the sample support to the ground and to align the sample support on the sample platform for analysis. In other instances, the electrical coupler engages the alignment coupler through a friction fit optionally with the use of an insert or adapter as described herein. In other instances, the alignment coupler comprises threads configured to couple to threads of the at least one aperture. If desired, the sample platform can include two or more apertures, e.g., a second aperture configured to electrically couple the sample support to the ground through an additional electrical coupler. Where more than one aperture is present, the sample holder assembly can include a first alignment coupler and a second alignment coupler, in which the first alignment coupler is configured to engage the electrical coupler and the second alignment coupler is configured to engage the additional electrical coupler to provide electrical coupling of the sample support to ground. As described herein, the sample holder assembly can also include orientation contacts, actuation contacts or other features to facilitate desired functionality of the sample holder assembly. In some embodiments, the various couplers described herein can be configured to provide electrical coupling between the sample support and the ground without the use of any threaded fasteners. By using non-threaded fasteners, the sample support can be quickly coupled to the sample platform for analysis of samples on the sample support and then easily removed and replaced with a different sample support comprising other samples.

In certain embodiments, a sample holder assembly comprising a sample platform comprising an electrical coupler configured to electrically couple a sample support to ground through an electrically conductive locating pin on the sample support, and an additional electrical coupler configured to couple to the electrical coupler of the sample platform and the electrical coupler of the sample support to provide electrical coupling between the sample support and the ground can be used. In certain examples, the platform can include a second electrical coupler that is configured to couple to a second electrically conductive locating pin on the sample support to electrically couple the sample support to the ground. In some embodiments, one or more inserts or adapters can be used. For example, a first adapter configured to couple to the electrical coupler and the first locating pin and a second adapter configured to couple to the second electrical coupler and the second locating pin to permit coupling of the sample support to the sample platform and provide electrical coupling between the sample platform and the ground can be present in the sample holder assembly. In some instances, the electrical coupler and the second electrical coupler are polarized to permit coupling of the sample support to the sample platform in a single orientation. In further embodiments, the sample platform can include an orientation contact on the sample platform to permit engagement of the sample support to the sample platform in a single orientation. If desired, an actuation contact may be present by itself or in combination with the orientation contact. In some instances, the actuation contact on the sample platform is configured to permit rotation of the sealing device up to about 180 degrees. If desired, the sample support holder can be configured to receive a sample for direct sample analysis, e.g., can comprise two or more plates that can sandwich a mesh material between them where the mesh material can retain a liquid sample or powder sample for at least some period to permit analysis of the sample using direct sample analysis. As described herein, the various components of the sample holder assembly can be configured to couple to each other through a friction fit or without the use of any threaded fasteners or threads on the components.

In certain examples, the sample holder assembly can include a sample platform configured to retain a sample support effective to retain a sample for direct sample analysis, the sample platform comprising at least one integral coupler configured to couple the sample platform to a sample support, an electrical coupler configured to couple to the at least one integral coupler of the sample platform and provide the electrical coupling of the sample support to ground, and an alignment coupler configured to engage to the electrical coupler to permit the electrical coupling of the sample support to the ground and to align the sample support on the sample platform. In some instances, the integral electrical coupler comprises stainless steel or other suitable substantially inert conductive materials. In some embodiments, the sample platform further comprises a second integral coupler configured to couple the sample support to the sample platform. In certain examples, the integral coupler and the second integral coupler can be sized differently to assist in proper coupling of the sample support to the sample platform. In other configurations, the integral coupler and the second integral coupler are substantially parallel to each other, e.g., can lie in the same plane or along the same axis such that the apertures of the sample support can be positioned in about the same plane. In some instances, the sample holder assembly can include a second electrical coupler configured to couple to the second integral coupler to provide electrical coupling of the sample support to the ground. In other embodiments, the integral coupler and the second integral coupler are sized substantially the same and the electrical coupler and the second electrical coupler are sized differently, e.g., to facilitate coupling of the sample support to the sample platform in a single orientation. In certain examples, the sample holder assembly can include a second alignment coupler configured to couple to the second electrical coupler to provide the electrical coupling of the second electrical coupler to the ground. If desired, the electrical coupler and the second electrical coupler are sized substantially the same and the alignment coupler and the second alignment coupler are sized differently. In other examples, the integral coupler and the second integral coupler are sized substantially the same, the electrical coupler and the second electrical coupler are sized differently and in which the alignment coupler is sized to engage to the electrical coupler and the second alignment coupler is sized to engage to the second electrical coupler to permit insertion of the sample holder into the sample support in a single orientation.

In other embodiments, the sample holder can include a sample support comprising a first coupler, and a sample platform comprising a first aperture configured to reversibly couple to the first coupler of the sample support, the aperture of the sample platform configured to align the sample support on the sample platform and provide electrical coupling of the sample support to ground. If desired, the sample support can further include a second coupler configured to electrically couple the sample support to ground, in which the sample platform comprises a second aperture configured to reversibly couple to the second coupler to provide electrical coupling of the sample support to the ground. If desired, the apertures may be sized and arranged to permit insertion of the sample support into the sample platform in a single orientation. In some instances, the sample platform comprises a removable alignment coupler configured to permit coupling of the sample support into the sample platform in a single orientation. In certain examples, the assembly can include an electrical coupler configured to electrically couple to the first coupler and the first aperture to permit electrical coupling of the sample support to the ground. In other embodiments, the sample support can also include a second coupler configured to electrically couple the sample support to ground, in which the sample platform comprises a second aperture configured to reversibly couple to the second coupler of the sample support to permit electrical coupling of the sample support to the ground, the sample holder assembly further comprising a first electrical coupler configured to electrically couple to the first coupler of the sample support and the first aperture of the sample platform to permit electrical coupling of the sample support to the ground and a second electrical coupler configured to electrically couple to the second coupler of the sample support and the second aperture of the sample platform to permit electrical coupling of the sample support to the ground. In some configurations, the various components may be sized and arranged differently to facilitate coupling of the sample support to the platform in a single orientation.

In some examples, the sample holder assemblies described herein can include a sample support comprising a first coupler configured to couple the sample support to a sample platform, a first electrical coupler configured to couple to the first coupler of the sample support, and a first alignment coupler configured to couple to the first electrical coupler and to the sample support to provide electrical coupling between the sample support and the ground. In some embodiments, the sample support is configured to retain a sample support configured for direct sample analysis, e.g., comprises two or more plates as described herein. In other embodiments, the sample support or the sample holder assembly can include one or more additional couplers each effective to couple the sample support to the sample platform.

In certain embodiments, the sample supports described herein may take many different configurations including those which include two or more plates that can couple to each other using fasteners, e.g., screws or springs, or through one or more hinges and or retaining devices as described in commonly assigned patent application entitled "Sample Holders and Methods of Using Them" and filed on Oct. 28, 2012 as U.S. Ser. No. 13/662,500, the entire disclosure of which is hereby incorporated herein by reference for all purposes. In brief, the sample support may be configured as a sample holder that can receive a mesh with an effective pore size to retain the sample. The pore size and configuration may be selected depending on the form of the sample to be loaded, e.g., liquid, solid, gas, supercritical fluid, etc. While the exact material of the sample support may vary, the sample support typically includes, or is made of, a substantially inert material so no interferences are created from the sample support material leaching or otherwise desorbing from the sample support. In some examples, the sample support can include substantially inert meshes such as, for example, stainless steel meshes, inert polymeric meshes, substantially inert membranes or membrane materials or combinations of any of them.

In a typical sampling operation, the sample can be added to the sample support, e.g., either directly or by suspending the sample in a liquid or dissolving the sample in a solvent, where it is retained at least for a sufficient period to permit analysis of the sample. Where the sample is a solid, it may be crushed, pulverized, homogenized or otherwise rendered into powder or crystalline form to be loaded onto the sample support. A diluent or carrier can be added to the powder to clump or agglomerate the powder to facilitate loading onto the sample support. Where diluents or carriers are used, suitable materials are selected so they do not create species that may interfere with any analysis of the sample. Where the sample is a liquid, it may be sprayed on, dropped on, pipetted on or otherwise introduced onto the sample support. In some embodiments, the sample support can be dipped into a liquid or liquids to load the samples onto the sample support. For example, the sample support can be configured with individual sections that are separated by openings and configured to be dipped or disposed into an individual receptacle, e.g., an individual microwell, to permit dipping of the sample support into a plurality of wells in a microwell plate. Such sample supports would permit automated sample loading and decrease the overall time needed to load samples onto the sample support.

Figure 14:
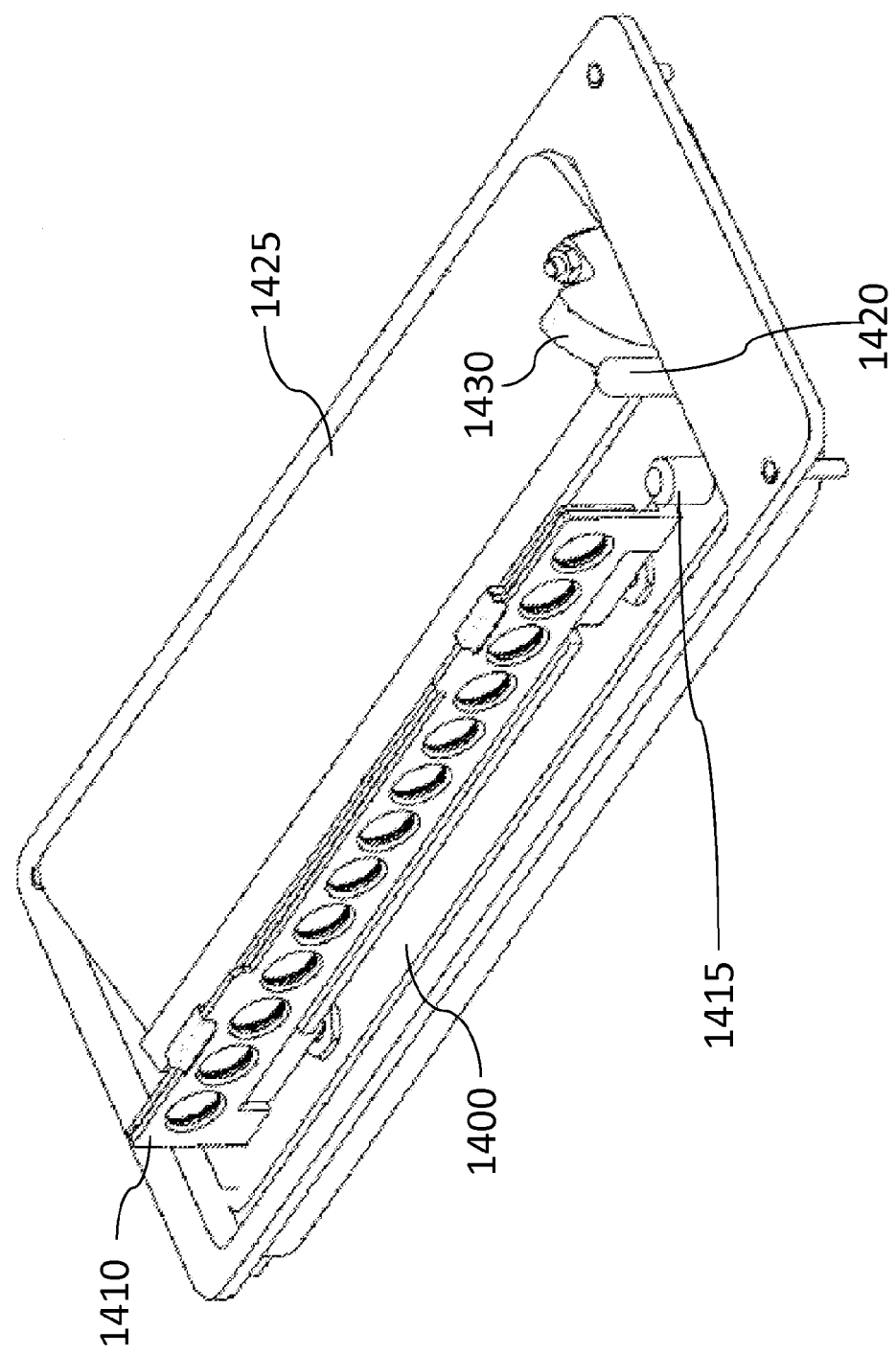
FIG. 14 is an illustration showing a sealing device, in accordance with certain examples.
Figure 15:
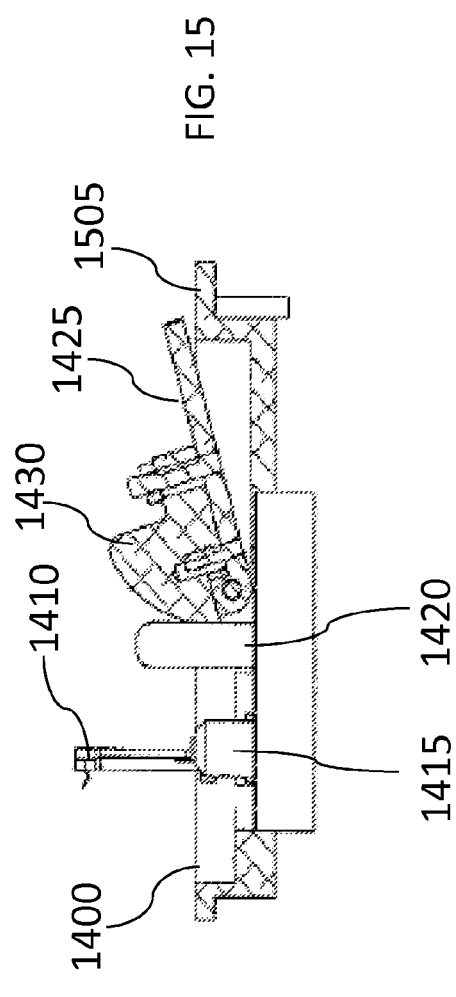
FIG. 15 is a side view of the illustration of FIG. 14, in accordance with certain examples.

In certain embodiments, the sample support can then be coupled to the sample platform as described herein. An illustration of a sample support coupled to the platform is shown in FIG. 14. A sample support 1410 is shown coupled to a sample platform 1400 through two apertures and a pair of couplers. On the upper surface of the platform 1400 is an optional orientation contact 1415 and an actuation contact 1420, which is configured to engage a cam 1430 of a sealing device 1425. In use of the sample holder assembly, the platform 1400 is raised using a motor or other actuation device to permit loading of the sample support 1410 onto the platform 1400. As the platform is raised, the actuation contact 1420 engages the cam 1430 on the sealing device 1425, which acts to rotate the sealing device 1425, e.g., about 180 degrees, and permit access to the platform 1400. A side view of FIG. 14 is shown in FIG. 15. The sealing device 1425, which can be configured as a door or cover, is shown in an open position resting against a stop 1505. A spring mechanism may be present to keep the sealing device 1425 in the closed position until the cam 1430 engages the actuation contact 1420 on the sample platform 1400. The sample holder with loaded samples is then placed into an instrument for analysis by lowering the sample platform and translating the sample platform with coupled sample support to a desired position within the instrument. As the platform 1400 is lowered for analysis, the actuation contact 1420 disengages the cam 1430 which permits the sealing device 1425 to rotate counterclockwise in the view shown in FIG. 14 to close and generally cover the opening.

In certain embodiments, the sample platforms, sample supports, couplers, inserts and other components of the sample platforms and sample holder assemblies described herein can be produced using one or more suitable materials that are generally inert so as to not substantially interfere with, or contaminate, any sample analysis. In some embodiments, the materials may be one or more plastic materials including thermoplastics and thermosets. In some embodiments, the plastic material desirably has a melting temperature of greater than 250 degrees Celsius, more particularly greater than 300 degrees Celsius. In certain embodiments, any one or more of the plates, retaining devices, joints, etc., of the sample holders described herein can include a thermoplastic comprising an acrylic polymer, a fluoroplastic polymer, a polyoxymethylene polymer, a polyacrylate polymer, a polycarbonate polymer, a polyethylene terephthalate polymer, a polyester polymer, a polyetheretherketone polymer, a polyamide polymer, a polyimide polymer, a polyamide-imide polymer, a polyaryletherketone polymer or combinations and copolymers thereof. If desired metallic or conductive particles can be included in the thermoplastic to facilitate electrical coupling of the sample support to an electrical ground. In some embodiments, the thermoplastic used is substantially transparent when viewed with the human eye to facilitate, for example, positioning of the sample support in the sample holder. In certain embodiments, the components of the sample holder assemblies can be produced using one or more substantially inert metal materials including, for example, Inconel® alloys, titanium and titanium alloys, aluminum and aluminum alloys, stainless steels, refractories or other suitable materials that include metals and which are substantially inert in the use environment of the sample holder assembly and sample platforms.

In certain embodiments, some components of the sample holder assemblies can be produced using materials other than inert materials if desired. For example, portions of the electrical couplers that are coupled to and within the apertures may generally be out of the fluid stream that contacts the sample and can be produced using materials other than non-inert materials. If desired, the different components of the assemblies can be produced using different materials.

In some embodiments, the components of the sample holder assemblies described herein can include a material that can withstand a cleaning operation such as, for example, sonication, solvent washes or other cleaners can be used to clean and/or remove any residue from the sample holder prior to reuse. In some configurations, the materials of the sample holder assemblies can withstand such washing steps and substantially no deterioration occurs after washing.

Figure 16:
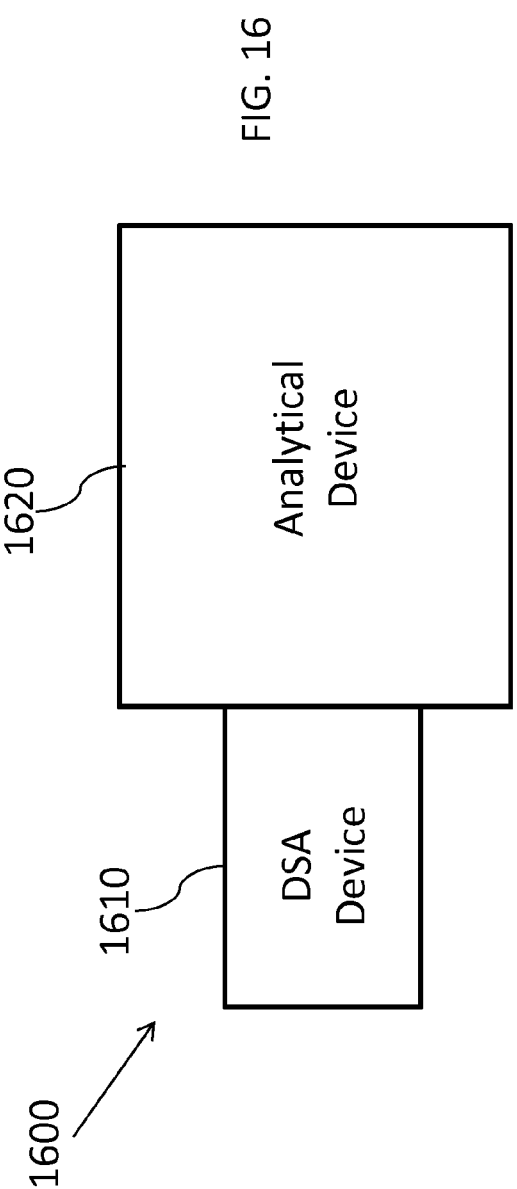
FIG. 16 is a block diagram of a system showing a direct sample analysis device coupled to an analytical device, in accordance with certain examples.

In some examples, the sample holder assemblies described herein may be used to permit direct sample analysis of a sample on the sample support loaded into the sample holder. An illustration of a system including a direct sample analysis device is shown in FIG. 16. The system 1600 generally comprises a direct sample analysis (DSA) device 1610 fluidically coupled to an analytical device 1620. In certain embodiments, the analytical device 1620 may take many forms including mass spectrometers, optical absorbance or emission detectors, plasma based analytical systems or other systems. In direct sample analysis, the sample can be directly analyzed without undergoing pre-sample preparation or purification, e.g., without being subjected to one or more purification steps, chromatographic separation steps or the like. In a typical operation, the sample is ionized after collision with an energized ion or atom, e.g., an electronically excited ion or atom. The collisional atoms are typically provided by an ion source such as, for example, an electron ionization source, a chemical ionization source, an electrospray ionization source, an atmospheric-pressure chemical ionization source, a plasma (e.g., inductively coupled plasma), glow discharge sources, field desorption sources, fast atom bombardment sources, thermospray sources, desorption/ionization on silicon sources, secondary ion mass spectrometry sources, spark ionization sources, thermal ionization sources, ion attachment ionization sources, photoionization or other suitable ion sources. Energy transfer can occur between excited molecules from the ion source and the sample which can cause ejection of charged sample species from the sample support. The ejected species may be provided to the analytical device 1620 or system, e.g., a mass analyzer, for detection. In a typical setup, the ions which are provided to the analytical device 1620 pass through an interface (not shown) which may include one or more ion guides or lenses to select an analyte of a desired mass-to-charge ratio and/or remove any interfering or unwanted species.

Figure 17:
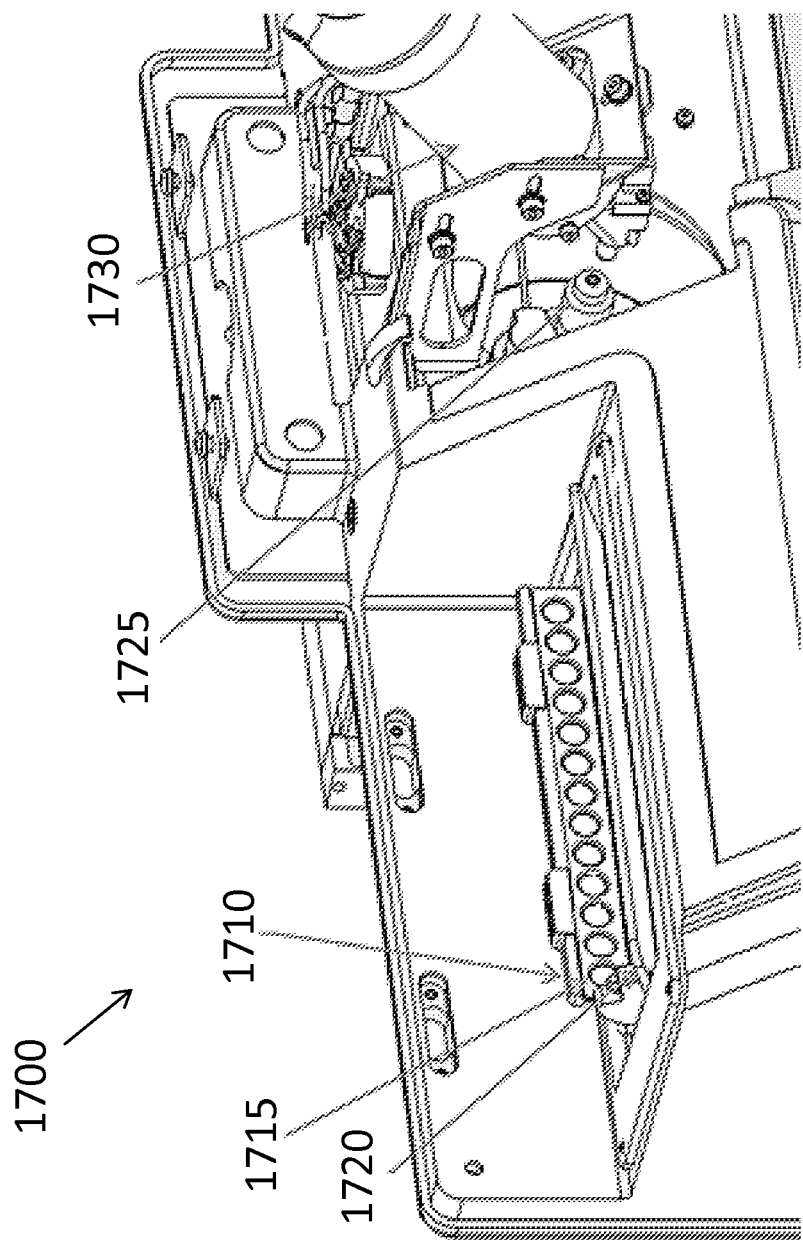
FIG. 17 is an illustration showing some components of a direct sample analysis device with the sealing device in the open position, in accordance with certain examples.
Figure 18:
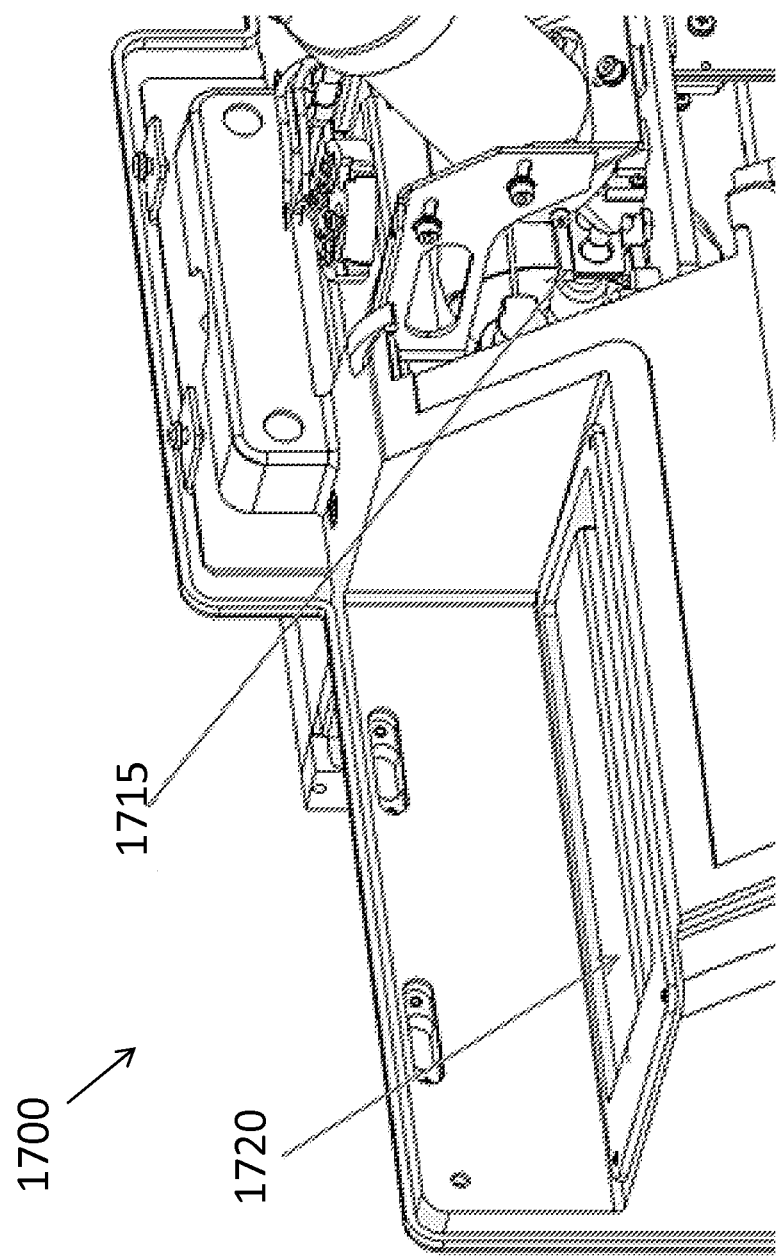
FIG. 18 is an illustration showing some components of a direct sample analysis device of FIG. 17 with the sealing device in the closed position, in accordance with certain examples.

In certain examples, an illustration of a DSA device is shown in FIGS. 17 and 18. Referring to FIG. 17, the DSA device 1700 includes a sample holder assembly 1710 including a sample support 1715 coupled to a sample platform. A sealing device 1720 is shown as being present in an open position to permit loading of the sample support 1715 onto the sample platform. The DSA device 1700 also comprises a lens assembly 1725 and an ion source or gun 1730. Referring also to FIG. 18, once the sample support 1715 is loaded, the sample platform is lowered into the DSA device 1700 and moved toward the right of the figure to align one of the apertures of the sample support 1715 with the ion gun 1730 and the lens assembly 1725. Ions from the ion gun 1730 impact the sample on the sample support 1715, and ionized sample exits the sample support on an opposite side of the sample support 1715 and enters the lens assembly 1725. As shown in FIG. 18, the sealing device 1720, e.g., a cover, is in the closed position during analysis of the sample. The sealing device rotates about 150-180 degrees from its open position in FIG. 17 to the closed position in FIG. 18 to generally cover the opening of the DSA device 1700. The lens assembly 1725 may be fluidically coupled to the analytical device 1620 to provide ionized sample from the DSA device to the analytical device 1620.

In certain embodiments where the analytical device 1620 takes the form of a mass spectrometer, many different types of mass analyzers can be used with the sample support holders described herein. For example, sector field mass analyzers, time of flight mass analyzers, quadrupole mass filters, ion traps, linear quadrupole ion traps, orbitraps or cyclotrons, e.g., Fourier transform ion cyclotron resonance or other suitable mass analyzers can be used. As selected ions exit the mass analyzer they can be provided to a detector to detect a change in charge or a current that is produced as the ions impact or travel by a surface, for example. Illustrative detectors include, but are not limited to, electron multipliers, Faraday cups, ion-to-photon detectors, microchannel plate detectors, an inductive detector or other suitable detectors may be used. The mass spectrometer typically will include a display that can provide a spectrum for review by the user. While not described, the mass spectrometer typically would include numerous other components including a vacuum system, one or more interfaces and many other components commonly found in mass spectrometers in use.

In certain embodiments, the components described herein can be packaged or group into a kit. In some examples, a kit comprising a sample platform configured to retain a sample support effective to retain a sample for direct sample analysis, the sample platform comprising a first integral coupler configured to couple the sample platform to the sample support to provide electrical coupling between the sample holder and ground can be provided. In some instances, the kit can include a first electrical coupler configured to couple to the first coupler of the sample platform to provide the electrical coupling between the sample support and the ground. In other embodiments, the sample platform of the kit further comprises a second coupler configured to provide electrical coupling between the sample support and the ground. In some examples, the kit can include a first electrical coupler configured to couple to the first coupler of the sample platform, and a second electrical coupler configured to couple to the second coupler of the sample platform, each of the first and second electrical couplers configured to permit electrical coupling between the sample support and the ground. In other examples, the kit can include an insert configured to couple to at least one of the first electrical coupler and the second electrical coupler. In certain embodiments, the sample platform of the kit comprises a first aperture configured to couple to the first electrical coupler and a second aperture configured to couple to the second electrical coupler. In other examples, the kit can include a first insert configured to couple to the first aperture and the first electrical coupler. In some embodiments, the kit can include a second insert configured to couple to the second aperture and the second electrical coupler. In certain examples, the first insert and the second insert are sized differently to permit coupling of the sample support to the sample platform in a single orientation. In other embodiments, the sample platform of the kit further comprises an actuation contact configured to engage a sealing device.

In certain embodiments, the sample holder assemblies described herein may be used for direct sample analysis to analyze a sample. In certain examples, the method can include providing a sample platform comprising a first integral coupler configured to provide electrical coupling between a sample support coupled to the sample platform and ground. In some embodiments, the method can include providing a first electrical coupler configured to couple to the first integral coupler and permit electrical coupling between the sample support and the ground. In other embodiments, the method can include providing the sample platform with a second integral coupler configured to provide electrical coupling between the sample support and ground. In some examples, the method can include providing a first electrical coupler configured to couple to the first integral coupler and a second electrical coupler configured to couple to the second integral coupler, each of the first and second electrical coupler configured to permit electrical coupling between the sample support and the ground. In other embodiments, the method can include providing an insert configured to couple to at least one of the first electrical coupler and the second electrical coupler. In some examples, the method can include providing the sample platform comprising a first aperture configured to couple to the first electrical coupler and a second aperture configured to couple to the second electrical coupler. In certain embodiments, the method can include providing a first insert configured to couple to the first aperture and the first electrical coupler. In some examples, the method can include providing a second insert configured to couple to the second aperture and the second electrical coupler. In further examples, the method can include providing a first insert and a second insert sized differently than the first insert to permit coupling of the sample support to the sample platform in a single orientation. In certain examples, the provided sample platform further comprises an actuation contact configured to engage a sealing device.

In some instances, a method comprising providing a sample support with at least one coupler configured to reversibly couple the sample support to a sample platform to provide electrical coupling of the sample support to ground can be performed. In certain embodiments, the method can include providing the ground to the sample support without using any threaded fasteners to couple the sample support to the sample platform. In other embodiments, the method can include providing a sample platform comprising an aperture configured to couple to the at least one coupler of the sample support. In certain examples, the method can include providing at least one electrical insert configured to couple to the at least one coupler and the aperture of the sample platform to provide electrical coupling between the sample support and the ground. In some embodiments, the method can include configuring the sample support with at least one additional coupler configured to reversibly couple the sample support to a sample platform and provide the electrical coupling between the sample support and the ground. In additional examples, the method can include providing a first electrical insert and a second electrical insert each configured to couple to one of the least one coupler and the additional coupler. In other embodiments, the method can include providing a sample platform comprising a first aperture configured to couple to the at least one coupler of the sample support and a second aperture configured to couple to the additional coupler of the sample support. In some instances, the method can include configuring the sample platform with an orientation contact to permit coupling of the sample support to the sample platform in a single orientation. In other embodiments, the method can include configuring the sample platform with an actuation contact that is configured to engage a sealing device. In some embodiments, the actuation contact is configured to permit rotation of the sealing device up to about 180 degrees.

When introducing elements of the aspects, embodiments and examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

The invention claimed is:

1. A sample holder assembly for use in direct sample analysis, the sample holder assembly comprising:
   a sample platform configured to retain a sample support effective to retain a sample for direct sample analysis, the sample platform comprising at least one aperture, the sample platform further comprising an orientation contact projecting from a surface of the sample platform and configured to engage a rear surface of the sample support to position the sample support on the sample platform, the sample platform further comprising an actuation contact configured to engage a sealing device as the sample platform is raised to permit loading of sample on or in the sample support, the actuation contact further configured to disengage the sealing device when the sample platform is lowered to permit analysis of sample loaded into the sample support; and
   an electrical coupler integral to the sample support and configured to couple to the sample platform through the at least one aperture of the sample platform to retain the sample support on the sample platform and provide electrical coupling of the sample support to ground.

2. The sample holder assembly of claim 1, in which the electrical coupler is configured to engage an alignment coupler on the sample platform, the alignment coupler configured to electrically couple the sample support to the ground and to align the sample support on the sample platform for analysis.

3. The sample holder assembly of claim 2, in which the electrical coupler engages the alignment coupler through a friction fit to retain the sample support to the sample platform.

4. The sample holder assembly of claim 2, in which the alignment coupler comprises threads configured to couple to threads of the at least one aperture.

5. The sample holder assembly of claim 1, further comprising a second aperture on the sample platform, in which the second aperture is configured to electrically couple the sample support to the ground through a second electrical coupler on the sample support.

6. The sample holder assembly of claim 5, in which the sample holder assembly further comprises a first alignment coupler and a second alignment coupler, in which the first alignment coupler is configured to engage the electrical coupler and the second alignment coupler is configured to engage the second electrical coupler to provide electrical coupling of the sample support to ground.

7. The sample holder assembly of claim 1, in which the orientation contact on the sample platform and the actuation contact on the sample platform are adjacent to each other at a same end of the sample platform.

8. The sample holder assembly of claim 1, in which the actuation contact is configured as a pin.

9. The sample holder assembly of claim 8, in which the actuation contact on the sample platform is configured to permit rotation of the sealing device up to about 180 degrees.

10. The sample holder assembly of claim 1, in which the electrical coupler is configured to provide the electrical coupling between the sample support and the ground without the use of any threaded fasteners.

11. A sample holder assembly comprising:
a sample platform comprising an aperture configured to receive a first electrical coupler, the first electrical coupler configured to electrically couple a sample support to ground through first electrically conductive locating pin on the sample support, the sample platform further comprising an orientation contact projecting from a surface of the sample platform and configured to engage a rear surface of a sample support reversibly coupled to the sample platform to position the sample support on the sample platform, the sample platform further comprising an actuation contact configured to engage a sealing device as the sample platform is raised to permit loading of sample on or in the sample support, the actuation contact further configured to disengage the sealing device when the sample platform is lowered to permit analysis of sample loaded into the sample support; and
a second electrical coupler configured to couple to the first electrical coupler of the sample platform and the first electrically conductive locating pin of the sample support to provide electrical coupling between the sample support and the ground.

12. The sample holder assembly of claim 11, further comprising a third electrical coupler on the sample platform that is configured to couple to a second electrically conductive locating pin on the sample support to electrically couple the sample support to the ground, in which the second electrically conductive locating pin on the sample support is separate from the electrically conductive locating pin om the sample support.

13. The sample holder assembly of claim 12, further comprising a first adapter configured to couple to the first electrical coupler and the first electrically conductive locating pin and a second adapter configured to couple to the second electrical coupler and the second electrically conductive locating pin to permit coupling of the sample support to the sample platform and provide electrical coupling between the sample platform and the ground.

14. The sample holder assembly of claim 12, in which the first electrical coupler and the second electrical coupler are polarized to permit coupling of the sample support to the sample platform in a single orientation.

15. The sample holder assembly of claim 12, in which the first electrical coupler is configured to sit flush with a planar surface of the sample platform when the first electrical coupler is fully inserted into the aperture of the sample platform.

16. The sample holder assembly of claim 15, in which the first electrical coupler comprises a lip configured to sit above a planar surface of the sample platform when the first electrical coupler is fully inserted into the aperture of the sample platform.

17. The sample holder assembly of claim 16, in which the actuation contact on the sample platform is configured to permit rotation of the sealing device up to about 180 degrees.

18. The sample holder assembly of claim 11, in which the sample support is configured to receive a sample for direct sample analysis.

19. The sample holder assembly of claim 11, in which the first electrical coupler of the sample platform is configured to engage the first electrically conductive locating pin of the sample support through a friction fit between an aperture of the first electrical coupler and the sample support and the first electrically conductive locating pin.

20. The sample holder assembly of claim 11, in which the first electrical coupler of the sample platform is configured to provide the electrical coupling between the sample support and the ground without the use of any threaded fasteners.

* * * * *